US008202886B2

(12) United States Patent
Cress et al.

(10) Patent No.: US 8,202,886 B2
(45) Date of Patent: Jun. 19, 2012

(54) SMALL MOLECULE E2F INHIBITOR

(75) Inventors: Douglas W. Cress, Lutz, FL (US);
Yihong Ma, Lutz, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 29 days.

(21) Appl. No.: 12/872,263

(22) Filed: Aug. 31, 2010

(65) Prior Publication Data
US 2011/0053977 A1 Mar. 3, 2011

Related U.S. Application Data

(63) Continuation of application No. PCT/US2009/037510, filed on Mar. 18, 2009.

(60) Provisional application No. 61/037,547, filed on Mar. 18, 2008.

(51) Int. Cl.
*A61K 31/4709* (2006.01)
(52) U.S. Cl. ........................................ 514/314
(58) Field of Classification Search .................. 514/314
See application file for complete search history.

(56) References Cited

FOREIGN PATENT DOCUMENTS
| | | |
|---|---|---|
| EP | 1350514 A2 | 8/2003 |
| WO | 9716443 A1 | 5/1997 |
| WO | 03091432 A1 | 11/2003 |
| WO | 03102026 A1 | 12/2003 |

OTHER PUBLICATIONS

Morissette et al. (Advanced Drug Delivery Reviews, vol. 56, pp. 275-300; 2004).*
Vippagunta et al. (Advanced Drug Delivery Reviews, vol. 48, Abstract; 2001).*
You et al. (Biochemical and Biophysical Research Communications, vol. 407, pp. 1-6; 2011).*
Nevins (Human Molecular Genetics, vol. 10, No. 7, pp. 699-703; 2001).*
Dyson, The Regulation of E2F by pRB-Family Proteins, Genes & Development, 1998, vol. 12, pp. 2245-2262.
Tao et al., Subunit Composition Determines E2F DNA-Binding Site Specificity, Molecular and Cellular Biology, 1997, vol. 17, No. 12, pp. 6994-7007.
International Search Report for PCT/US2009/037510 dated Dec. 16, 2009.
Dupree et al., Genotoxic Stress Induces Expression of E2F4, Leading to Its Association with p130 in Prostate Carcinoma Cells, Cancer Research, 2004, vol. 64, pp. 4390-4393.
Verona et al., E2F Activity Is Regulated by Cell Cycle-Dependent Changes in Subcellular Localization, Molecular and Cellular Biology, 1997, vol. 17, No. 12, pp. 7268-7282.
Moberg et al., E2F-4 Switches from p130 to p107 and pRB in Response to Cell Cycle Reentry, Molecular and Cellular Biology, 1996, vol. 16, No. 4, pp. 1436-1449.
Wu et al., Expression of Dominant-Negative Mutant DP-1 Blocks Cell Cycle Progression in G1, Molecular and Cellular Biology, 1996, vol. 16, No. 7, pp. 3698-3706.
Ma et al., Regulation of the Cyclin D3 Promoter by E2F1, The Journal of Biological Chemistry, 2003, vol. 278, No. 19, pp. 16770-16776.
Montigiani et al., Inhibition of Cell Proliferation and Induction of Apoptosis by Novel Tetravalent Peptides Inhibiting DNA Binding of E2F, Oncogene, 2003, vol. 22, pp. 4943-4952.
Fabbrizio et al., Inhibition of Mammalian Cell Proliferation by Genetically Selected Peptide Aptamers that Functionally Antagonize E2F Activity, Oncogene, 1999, vol. 18, pp. 4357-4363.
He et al., Identification of E2f-3B, an Alternative Form of E2F-3 Lacking a Conserved N-Terminal Region, Oncogene, 2000, vol. 19, pp. 3422-3433.
Croxton et al., Differences in DNA Binding Properties Between E2F1 and E2F4 Specify Repression of the Mcl-1 Promoter, Oncogene, 2002, vol. 21, pp. 1563-1570.
Crosby et al., Opposing Roles of E2Fs in Cell Proliferation and Death, Cancer Biology & Therapy, 2004, vol. 3, No. 12, pp. 1208-1211.
Ma et al., E2F4 Deficiency Promotes Drug-Induced Apoptosis, Cancer Biology & Therapy, 2004, vol. 3, No. 12, pp. 1262-1269.
Ma et al., Flavopiridol-Induced Apoptosis Is Mediated Through Up-Regulation of E2F1 and Repression of Mcl-1, Molecular Cancer Therapeutics, 2003, vol. 2, pp. 73-81.
Lin et al., Selective Induction of E2F1 in Response to DNA Damage, Mediated by ATM-Dependent Phosphorylation, Genes & Development, 2001, vol. 15, pp. 1833-1844.
Zheng et al., Structural Basis of DNA Recognition by the Heterodimeric Cell Cycle Transcription Factor E2F-DP, Genes & Development, 1999, vol. 13, pp. 666-674.
Siddiquee et al., Selective Chemical Probe Inhibitor of Stat3, Identified Through Structure-Based Virtual Screening, Induces Antitumor Activity, PNAS, 2007, vol. 104, No. 18, pp. 7391-7396.

(Continued)

*Primary Examiner* — Phyllis G. Spivack
*Assistant Examiner* — Nelson C Blakely, III
(74) *Attorney, Agent, or Firm* — Michele L. Lawson; Smith & Hopen, P.A.

(57) ABSTRACT

A small molecular inhibitor of E2F (HLM006474) was identified using a computer-based virtual screen and the known crystal structure of the DNA bound E2F4/DP2 heterodimer. Treatment of multiple cell lines resulted in the loss of intracellular E2F4 DNA-binding activity. Overnight exposure to HLM006474 resulted in down regulation of total E2F4 protein as well as several known E2F targets. The effects of treatment on different cell lines included a reduction in cell proliferation and an increase in apoptosis. Apoptosis was induced in a manner distinct from cisplatin and doxorubicin. E2F4-null MEFs (mouse embryo fibroblasts) were less sensitive than wildtype counterparts to the apoptosis-inducing activity of the compound revealing its biological specificity. A375 cells were extremely sensitive to the apoptosis-inducing activity of the compound in two-dimensional culture and HLM006474 was a potent inhibitor of melanocytes proliferation and subsequent invasion in a three-dimensional tissue culture model system.

10 Claims, 25 Drawing Sheets

OTHER PUBLICATIONS

Ikeda et al., A Unique Role for the Rb Protein in Controlling E2F Accumulation During Cell Growth and Differentiation, Proc. Natl. Acad. Sci. USA, 1996, vol. 93, pp. 3215-3220.

Halgren et al., Glide: A New Approach for Rapid, Accurate Docking and Scoring. 2. Enrichment Factors in Database Screening, J. Med. Chem., 2004, vol. 47, pp. 1750-1759.

Friesner et al., Glide: A New Approach for Rapid, Accurate Docking and Scoring. 1. Method and Assessment of Docking Accuracy, J. Med. Chem., 2004, vol. 47, pp. 1739-1749.

Berry et al., Retinoblastoma Protein Inhibits IFN-gamma Induced Apoptosis, Oncogene, 1996, vol. 12, No. 8, pp. 1809-1819.

Brooks et al., Computational Validation of the Importance of Absolute Stereochemistry in Virtual Screening, J. Chem. Inf. Model., 2008, vol. 48, pp. 639-645.

Eblen et al., Conditional Binding to and Cell Cycle-Regulated Inhibition of Cyclin-Dependent Kinase Complexes by p27Kip1, Cell Growth & Differentiation, 1995, vol. 6, pp. 915-925.

Sage, Hope In Sight for Retinoblastoma, Nature Medicine, 2007, vol. 13, No. 1, pp. 30-31.

Kong et al., Compensation and Specificity of Function Within the E2F Family, Oncogene, 2007, vol. 26, pp. 321-327.

La Thangue, The Yin and Yang of E2F-1: Balancing Life and Death, Nature Cell Biology, 2003, vol. 5, No. 7, pp. 587-589.

Macleod et al., Loss of Rb Activates Both p53-Dependent and Independent Cell Death Pathways in the Developing Mouse Nervous System, The EMBO Journal, 1996, vol. 15, No. 22, pp. 6178-6188.

Salama et al., A Review of the S100 Proteins in Cancer, EJSO The Journal of Cancer Surgery, 2008, vol. 34, pp. 357-364.

Bandara et al., Apoptosis Induced in Mammalian Cells by Small Peptides that Functionally Antagonize the Rb-Regulated E2F Transcription Factor, Nature Biotechnology, 1997, vol. 15, pp. 896-901.

Crosby et al., E2F4 Regulates a Stable G2 Arrest Response to Genotoxic Stress in Prostate Carcinoma, Oncogene, 2007, vol. 26, pp. 1897-1909.

Harbour et al., Rb Function in Cell-Cycle Regulation and Apoptosis, Nature Cell Biology, 2000, vol. 2, pp. E65-E67.

Johnson et al., Putting the Oncogenic and Tumor Suppressive Activities of E2F into Context, Current Molecular Medicine, 2006, vol. 6, pp. 731-738.

Thompson et al., Association of Increased Basement Membrane Invasiveness with Absence of Estrogen Receptor and Expression of Vimentin in Human Breast Cancer Cell Lines, Journal of Cellular Physiology, 1992, vol. 150, pp. 534-544.

Hazlehurst et al., Multiple Mechanisms Confer Drug Resistance to Mitoxantrone in the Human 8226 Myeloma Cell Line, Cancer Research, 1999, vol. 59, pp. 1021-1028.

Rempel et al., Loss of E2F4 Activity Leads to Abnormal Development of Multiple Cellular Lineages, Molecular Cell, 2000, vol. 6, pp. 293-306.

Bild et al., Oncogenic Pathway Signatures in Human Cancers as a Guide to Targeted Therapies, Nature, 2006, vol. 439, pp. 353-357.

Ma et al., Transcriptional Upregulation of p57 (Kip2) by the Cyclin-Dependent Kinase Inhibitor BMS-387032 is E2F Dependent and Serves as a Negative Feedback Loop Limiting Cytotoxicity, Oncogene, 2007, vol. 26, pp. 3532-3540.

Trimarchi et al., Sibling Rivalry in the E2F Family, Molecular Cell Biology, 2002, vol. 3, pp. 11-20.

Croxton et al., Direct Repression of the Mcl-1 Promoter by E2F1, Oncogene, 2002, vol. 21, pp. 1359-1369.

Dalton et al., Immunohistochemical Detection and Quantitation of P-Glycoprotein in Multiple Drug-Resistant Human Myeloma Cells: Association With Level of Drug Resistance and Drug Accumulation, Blood, 1989, vol. 73, No. 3, pp. 747-752.

* cited by examiner

Synthesis of HLM006474

H292 cells

H1299 cells

SMALL MOLECULE E2F INHIBITOR

CROSS REFERENCE TO RELATED APPLICATIONS

This application is a continuation of prior filed International Application, Serial Number PCT/US2009/037510 filed Mar. 18, 2009, which claims priority to U.S. provisional patent application No. 61/037,547 filed Mar. 18, 2008, which are hereby incorporated by reference into this disclosure.

GOVERNMENT SUPPORT

This invention was made with government support under CA090489 awarded by the National Institutes of Health. The government has certain rights in the invention.

BACKGROUND OF THE INVENTION

The E2F/Rb pathway is central to the regulation of the mammalian cell cycle, and thus, it appears a reasonable target for the development of chemotherapeutic agents (see Sage J. Hope in sight for retinoblastoma. Nat Med 2007; 13:30-1; La Thangue N B. The yin and yang of E2F-1: balancing life and death. Nat Cell Biol 2003; 5:587-9; and Johnson D G, Degregori J. Putting the Oncogenic and Tumor Suppressive Activities of E2F into Context. Current molecular medicine 2006; 6:731-8). The E2F family is composed of nine members with various biological roles (see Kong L J, Chang J T, Bild A H, Nevins J R. Compensation and specificity of function within the E2F family. Oncogene 2007; Trimarchi J M, Lees J A. Sibling rivalry in the E2F family. Nat Rev Mol Cell Biol 2002; 3:11-20; and Crosby M E, Almasan A. Opposing roles of E2Fs in cell proliferation and death. Cancer Biol Ther 2004; 3:1208-11). E2F1 is the best studied member of the family and has been shown to have numerous and even opposing roles in cell growth control depending on the context of experimentation. In the context of drug-induced apoptosis of highly transformed cells, E2F1 is downstream target of the ATM/ATR signaling pathway and contributes significantly to the apoptotic activity of DNA damaging drugs and cyclin dependent kinase inhibitors (Lin W C, Lin F T, Nevins J R. Selective induction of E2F1 in response to DNA damage, mediated by ATM-dependent phosphorylation. Genes Dev 2001; 15:1833-44). In contrast, E2F4 (the most abundant member of the E2F family) contributes to survival in the context of treatment with chemotherapeutic drugs or cdk inhibitors (see Ma Y, Freeman S N, Cress W D. E2F4 Deficiency Promotes Drug-Induced Apoptosis. Cancer Biol Ther 2004; 3:1262-9; Ma Y, Cress W D, Haura E B. Flavopiridol-induced apoptosis is mediated through up-regulation of E2F1 and repression of Mcl-1. Mol Cancer Ther 2003; 2:73-81; DuPree E L, Mazumder S, Almasan A. Genotoxic stress induces expression of E2F4, leading to its association with p130 in prostate carcinoma cells. Cancer Res 2004; 64:4390-3; and Crosby M E, Jacobberger J, Gupta D, Macklis R M, Almasan A. E2F4 regulates a stable G(2) arrest response to genotoxic stress in prostate carcinoma. Oncogene 2006; 26:1897-909).

While individual members of the E2F family have specialized roles, a variety of complementary approaches have shown that down regulation of total intracellular E2F activity can lead to apoptosis, growth arrest or both (see Montigiani S, Muller R, Kontermann R E. Inhibition of cell proliferation and induction of apoptosis by novel tetravalent peptides inhibiting DNA binding of E2F. Oncogene 2003; 22:4943-52; Wu C L, Classon M, Dyson N, Harlow E. Expression of dominant-negative mutant DP-1 blocks cell cycle progression in G1. Mol Cell Biol 1996; 16:3698-706; Fabbrizio E, Le Cam L, Polanowska J, et al. Inhibition of mammalian cell proliferation by genetically selected peptide aptamers that functionally antagonize E2F activity. Oncogene 1999; 18:4357-63; and Bandara L R, Girling R, La Thangue N B. Apoptosis induced in mammalian cells by small peptides that functionally antagonize the Rb-regulated E2F transcription factor. Nat Biotechnol 1997; 15:896-901).

SUMMARY OF INVENTION

The invention of a preferred embodiment includes a method of treating a cellular proliferative disorder by administering a therapeutically effective amount of a small molecule inhibitor. The inventors have used the known crystal structure of the DNA bound E2F4/DP2 heterodimer to guide a computational screen for small molecules that might inhibit this interaction (Zheng N, Fraenkel E, Pabo C O, Pavletich N P. Structural basis of DNA recognition by the heterodimeric cell cycle transcription factor E2F-DP. Genes Dev 1999; 13:666-74). One small molecule, HLM006474 (hereinafter the "therapeutic compound"), emerged with biological activity. The examples contained herein characterize the therapeutic compound's biological activities in a number of commonly examined cancer cell lines. the therapeutic compound was particularly active against a melanocyte cell line, A375. In two-dimensional culture, A375 cells were extremely sensitive to the apoptosis-inducing activity of the compound and in a three-dimensional tissue culture model system the therapeutic compound was a potent inhibitor of A375 proliferation and invasion.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention includes methods for treatment of a proliferative cellular disorder including administration of an effective amount of a small molecular inhibitor of E2F. In an illustrative embodiment, the small molecular inhibitor down regulates E2F4. The small molecular inhibitor of a preferred embodiment is the therapeutic compound and has the structure:

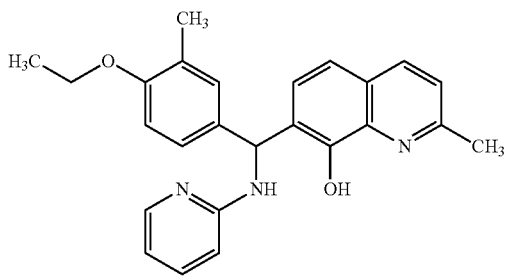

or a pharmaceutically acceptable salt, hydrate, or solvate thereof.

Figure 1:
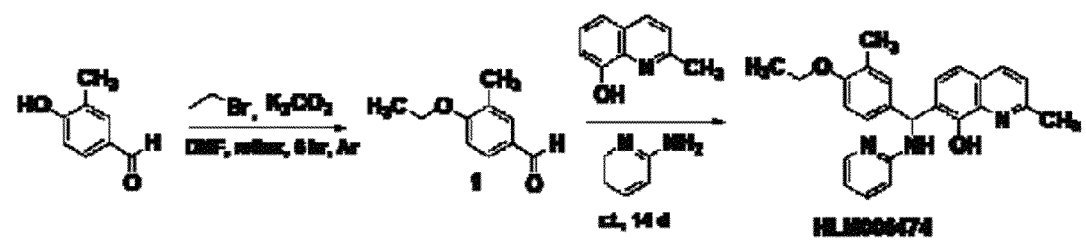
FIG. 1 shows the synthesis scheme and chemical structure of the therapeutic compound (Formula $C_{24}H_{25}N_3O_2$, MW 399.5).
Figure 3:
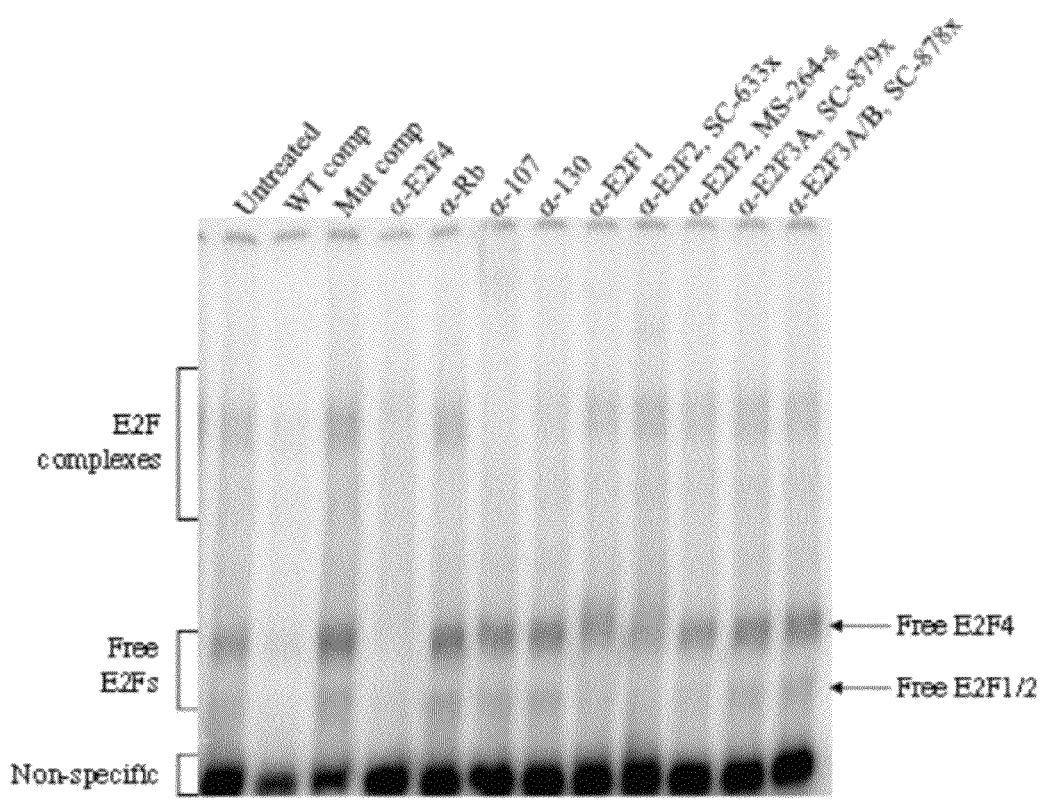
FIG. 3: E2F4 complexes represent the primary E2F activity in cellular extracts as measured in EMSA assays. The same untreated A375 cell extracts used in FIG. 1 were subjected to E2F EMSA assay including antibodies to identify specific complexes. The inhibitory antibodies or competitor oligonucleotides used are indicated. The arrow indicates the predominant free E2F4 band that is highlighted in FIGS. 1 and 10. E2F "complexes" are primarily represented by E2F4 in complex with p107 and p130. Other detectable free E2Fs include E2F1 and 2. The bottom band represents a non-specific complex. Data indicate that the predominant form of E2F present the A375 cell extracts (as measured using this probe) represents free E2F4.
Figure 4:
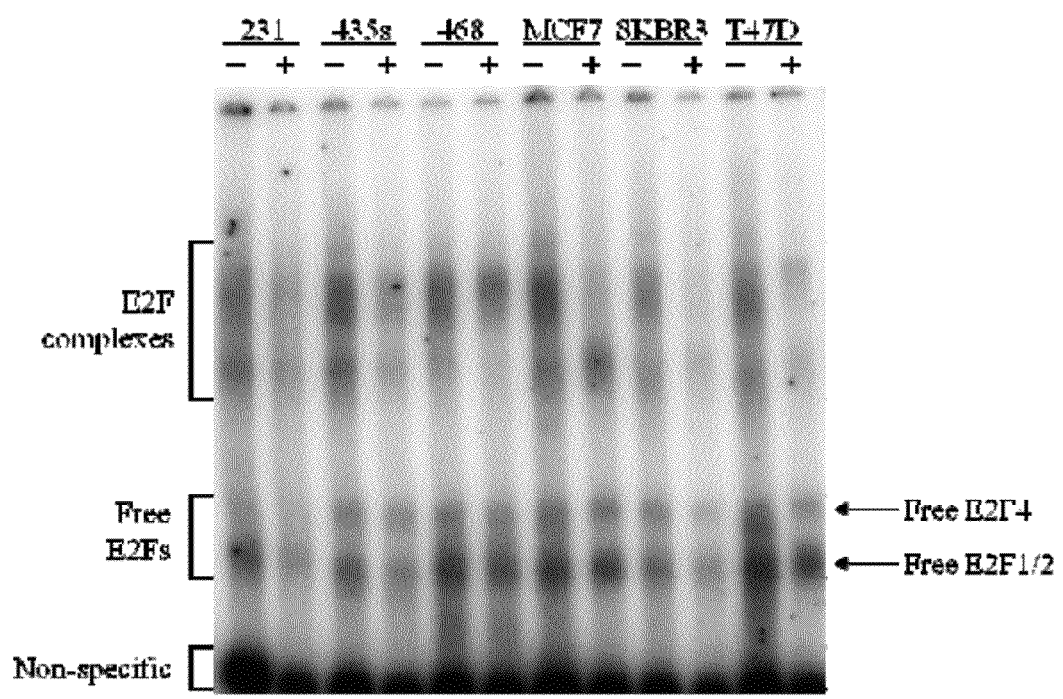
FIG. 4: HLM006474 targets all E2F complexes in EMSA assays. Several breast cancer cell lines were treated with 40 µM HLM006474 and extracts subjected to E2F EMSA assay. The upper bands (E2F complexes) represent trimeric E2F complexes including a DP1 dimerization partner and an Rb family member. The middle complexes (free E2F) represent free forms of E2F with the upper of these two bands representing E2F4. The bottom band represents a non-specific complex. Data indicate that all DNA-binding of all E2F complexes are inhibited by the therapeutic compound.

The therapeutic compound was synthesized at a large scale as a pure sample. The chemical synthesis and structure of the therapeutic compound are shown in FIG. 1. The therapeutic compound is not specific to E2F4 and appears to inhibit binding by all E2F complexes (see FIGS. 3 and 4). However, because E2F4 is the predominant E2F species present in cellular extracts, as measured by EMSA (FIG. 4), and because it has previously been shown that downregulation of E2F4 can predispose to chemotherapy-induced apoptosis (Ma et al., 2004), the following focuses on the biological activity of pure the therapeutic compound as it relates to inhibition of E2F4.

The molecular weight of the therapeutic compound=399.5 Da; Log P (theoretical)=5.45. A mixture of 4-Hydroxy-3-methyl benzaldehyde (0.9 g, 0.0066 mol), bromoethane (0.72 g, 0.0066 mol) and $K_2CO_3$ (9.13 g, 0.066 mol) was stirred in anhydrous dimethylforamide at 80° C. under inert atmosphere for 6 hr. The reaction was monitored by thin layer chromatography (t.l.c.) (40% ethyl acetate in hexane). The crude reaction mixture was poured into 300 ml of water, and extracted with dichloromethane (200 ml×2). The organic phase was washed with 200 ml of water, combined organics were dried ($MgSO_4$) and evaporated under reduced pressure to obtain the intermediate 1 (FIG. 1) as a dark brown solid (0.7 g, 65%). This intermediate was used in the next step without further purification. A mixture of intermediate 1 (0.343 g, 0.0021 mol), 2-Aminopyridine (0.197 g, 0.0021 mol) and 2-Methyl-8-quinolinol (0.333 g, 0.0021 mol) were dissolved in 10 ml of ethanol and stirred at room temperature for 2 weeks. The reaction was monitored by t.l.c (40% ethyl acetate in hexane).

The crude reaction mixture was dried under reduced pressure and purified by flash chromatography (ethyl acetate/hexane gradient elution) to provide pure the therapeutic compound as a white solid (0.103 g, 12%). $H^1$ NMR (400 MHz, DMSO-$d_6$) δ 8.13 (1H, d, J=8.8 Hz), 7.88 (1H, d, J=5.2 Hz), 7.50 (1H, d, J=8.8 Hz), 7.38 (1H, d, J=8.8 Hz), 7.34 (1H, dt, J=8.4, 1.6 Hz), 7.30 (1H, d, J=8.8 Hz), 7.24 (1H, NH, d, J=8.8 Hz, disappeared on $D_2O$ shake), 7.10 (1H, s), 7.07 (1H, dd, J=8.4, 2.0 Hz), 6.79 (1H, d, J=8.4 Hz), 6.68 (1H, CH, d, J=8.8 Hz), 6.62 (1H, d, J=8.4 Hz), 6.43 (1H, t, J=5.6 Hz), 5.85 (1H, OH, s), 3.94 (2H, $CH_2$, q, J=7.2 Hz), 2.67 (3H, $CH_3$, s), 2.06 (3H, $CH_3$, s), 1.28 (3H, $CH_3$, t, J=7.2 Hz). EIMS m/z [M+H]$^+$: 400.2009 (calcd. for $C_{25}H_{26}N_3O_2$, 400.2019); HPLC; 99% ($R_f$=2.35, 10% water in Methanol).

Here, the inventors show that this small molecule inhibitor of E2F activity has therapeutic efficacy in cancer. The inventors screened for compounds that inhibit E2F DNA-binding and identified one small molecule that clearly targets E2F and leads to significant downregulation of E2F4 protein. This unexpected activity may account for the primary biological activity and specificity of the therapeutic compound and provides an easy way to monitor its biological activity (E2F4 western blotting or IHC).

The terms "proliferative cellular disorder", "cancer", "cancerous", or "malignant" refer to or describe the physiological condition in mammals that is typically characterized by unregulated cell growth. Examples include, but are not limited to, melanomas, renal cancer, CNS cancer, leukemia, ovarian cancer, breast cancer, colon cancer and non-small cell lung cancer.

As used herein, the "modulate" refers to the activity of a compound to affect (e.g. promote or inhibit) an aspect of cellular function, including but not limited to gene expression, protein expression, protein activity, cell growth, proliferation, apoptosis and the like.

A therapeutically effective amount of the therapeutic compound or a pharmaceutically acceptable salt, hydrate, or solvate thereof refers to that amount being administered which will relieve, to some extent, one or more of the symptoms associated with the disorder being treated. In reference to the treatment of a proliferative cellular disorder, a therapeutically effective amount refers to the amount which: (1) reduces the size of a tumor, (2) inhibits (i.e. stopping or slowing to some extent) tumor metastasis, (3) inhibits (i.e. stopping or slowing to some extent) tumor growth, (4) inhibits (i.e. stopping or slowing to some extent) cellular proliferation, (5) inhibits (i.e. stopping or slowing to some extent) expression of any member of the E2F family and/or (6) inhibits (i.e. stopping or slowing to some extent) activity (e.g. DNA binding activity) of any member of the E2F family.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin EW [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The therapeutic compound is administered and dosed in accordance with good medical practice, taking into account the clinical condition of the individual patient, the site and method of administration, scheduling of administration, patient age, sex, body weight, and other factors known to medical practitioners.

Figure 2:
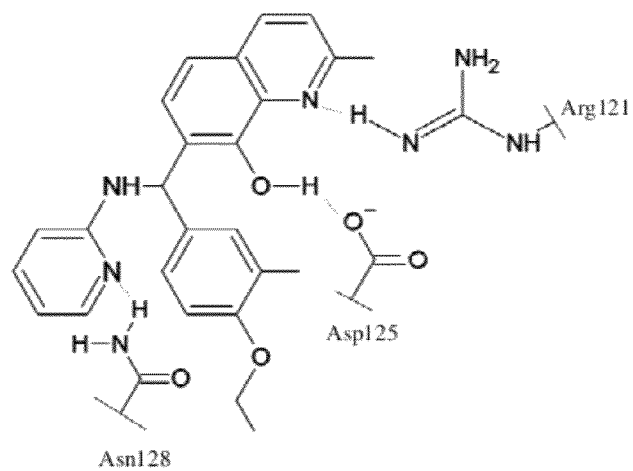
FIG. 2: Schematic showing the therapeutic compound forming hydrogen bonds with 3 residues (Asn 128, Asp 125, Arg 121) that are absolutely conserved within the E2F family.

The therapeutic compound is believed to make hydrogen bonds with three residues that are absolutely conserved within the E2F family (see FIG. 2), and thus, the therapeutic compound is not specific to E2F4 heterodimers. Indeed, FIGS. 3-8 demonstrate that essentially all E2F complexes detectable by standard EMSA assay are inhibited by the therapeutic compound. While the therapeutic compound is not specific to the DNA-binding domain of E2F4, experiments with E2F4 knockout MEFs demonstrate that cells which have presumably adapted to the absence of E2F4 (which has pro-survival activity) are less sensitive to the therapeutic compound than similarly-derived cells from littermate animals. This specificity is not trivial because E2F4-deficient MEFs are more sensitive to every drug the inventors have tested including flavopiridol, SNS-032, roscovitine, cisplatin and VP16. Although it does not formally rule out the possibility that other E2Fs are also important targets, this result strongly argues that the E2F4 is an important target for the therapeutic compound. This specificity may derive from HL006474's ability to lead to the downregulation of the E2F4 polypeptide.

It is known that a number of E2F-regulated promoters are primarily governed by transcriptional repression by E2F4/Rb family complexes during G0/G1; followed by depression at the G1/S boundary. Given this mechanism, it would be predicted that blocking E2F DNA-binding activity should result in upregulation of these genes, which might possibly result in increased cell growth. This effects the therapeutic conditions of E2F-targeted therapies. There is no evidence, however, that the therapeutic compound results in a net increase in cell growth in any cell line tested. However, only a subset of cell lines treated with the therapeutic compound are significantly growth inhibited at 40 µM (see FIGS. 6-7). Higher the therapeutic compound concentrations are more effective; however in order to limit off-target effects the examples provided below were conducted at 40 µM since it is just above the IC$_{50}$ of 29.8 µM (±7.6 µM). These results suggest that generating a net increase in tumor growth with E2F inhibitors is not likely; consistent with the literature (e.g. Montigiani et al., 2003, Wu et al., 1996, Fabbrizio et al., 1999 and Bandara et al. 1997).

Figure 9:
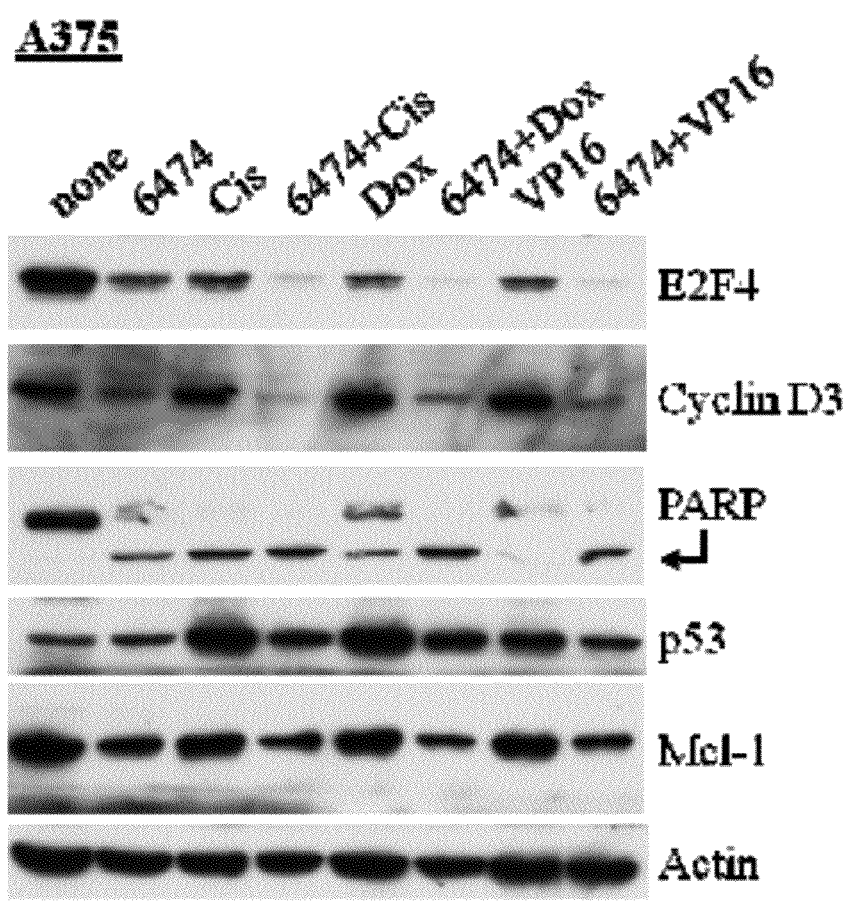
FIG. 9: HLM006474 treatment leads to apoptosis in a manner distinct from traditional chemotherapeutic drugs. A375 cells were treated 24-hrs with 40-μM HLM006474, 10 μM cisplatin, 10 nM doxorubicin or 10 μM VP16 or with combinations and Western analyses performed with the antibodies as indicated. The arrow highlights cleavage PARP, which can be an indicator of apoptosis.

The therapeutic compound clearly induces apoptosis in sensitive cell lines, such as A374 and 231 cells. The exact mechanism of "E2F-deficiency induced apoptosis" has not been adequately investigated. It has been shown that de-repression can be an important mechanism of E2F regulation (Macleod K F, Hu Y, Jacks T. Loss of Rb activates both p53-dependent and independent cell death pathways in the developing mouse nervous system. Embo J 1996; 15:6178-88), and it is straightforward to speculate that inhibition of E2F might lead to de-repression of cell death proteins. The inventors have previously demonstrated that E2F4 contributes significantly to survival during drug-induced apoptosis, and that several standard chemotherapeutic drugs significantly reduce E2F4 expression (Ma et al., 2004). FIG. 9 reveals that the therapeutic compound synergizes with cisplatin, doxorubicin and VP16 to reduce E2F4 levels. The inventors hypothesize that E2F deficiency-induced apoptosis is primarily the result of down regulation of E2F4's pro-survival role. At this point the key E2F target that may mediate this effect is unclear. P53 does not appear to play a role (FIG. 9), Mcl-1 is modestly down regulated in A375 cells following the therapeutic compound treatment (FIG. 9), which could account for the cells sensitivity to the compound. Likewise, pRb and p107 are down regulated following the therapeutic compound treatment (not shown). Since Rb family members are known to have prosurvival roles it is possible that their down regulation may contribute to cell death.

Although the biochemical mechanisms of the therapeutic compound action and specificity remain to be fully elucidated, this compound has significant biological activity that targets E2F4. The biological activity of the therapeutic compound is demonstrated most convincingly in a three-dimensional model of melanocyte proliferation and invasion. This example highlights the ability of the therapeutic compound to inhibit the proliferation and subsequent invasion of A375 melanocytes into an underlying dermal substrate. This model further demonstrates that the therapeutic compound reduces the levels of E2F4 in the treated melanocytes and that the reduction of E2F4 resulted in a significant decrease in cellular proliferation as measured by Ki-67 staining. Surprisingly, this model did not detect significant levels of apoptosis (as measured by activated caspase 3 IHC) in the treated versus control melanocytes; even though the compound induced significant apoptosis in two-dimensional culture. One explanation for this observation is that the apoptotic cells are simply not detected efficiently by the assay in 3D. Alternatively, it is possible that the apoptosis-inducing activity of the therapeutic compound is limited in 3D culture due to survival contacts present there and that the main biological activity of the therapeutic compound is indeed the ability to inhibit cell cycle progression. In either event, the following results provide strong evidence that E2F inhibitors have therapeutic potential in the appropriate context.

EXAMPLES

Cell Lines and Drug Treatments

3T3 immortalized mouse embryo fibroblasts (MEFS) derived from littermate wild type and E2F4 knock out mice were a gift from Drs. Rachel Rempel and Joseph Nevins (Duke University) and were grown in DMEM with 15% FBS. All human cell lines were originally obtained from the ATCC. The melanoma cell line A375 was a gift from Dr. Subhra Mohapatra (Moffitt Cancer Center, Tampa, Fla.) and was cultured in RPMI 1640 containing 10% fetal bovine serum. SK-BR3 were cultured in McCoy's 5A medium with 10% FBS. All other cell lines (MDA-MB-231, MDA-MB-435s, MDA-MB-468, MCF7, T47D and HFFs) were cultured in DMEM-F12 supplemented with 2 mM L-glutamine, 10% FBS and 1% P/S. VP16, cisplatin and doxorubicin were purchased from Sigma. VP-16 and the therapeutic compound were prepared in dimethylsulfoxide (DMSO), cisplatin in dimethylformamide, and doxorubicin in water. Control cells received an equal concentration of carrier, never exceeding 1%.

The 8226-s cells were grown as a suspension in RPMI 1640, supplemented with: 5% FBS; 1% (v/v) penicillin; (100 units/ml), streptomycin (100 µg/ml); and 1% (v/v) L-glutamine. 8226-dox40 and 8226-MR20 cell lines were cultured in the same medium with additional supplementary of doxorubicin and mitoxantrone respectively as descried previously. Doxorubicin was purchased from Sigma (D-1515) and mitoxantrone was a gift from Dr. Hazlehurst.

The following cell lines were used:
3T3 MEFS: immortalized mouse embryo fibroblasts (MEFS) derived from littermate wild type and E2F4 knock out mice, a gift from Joe Nevins at Duke University.
A375: human melanocyte cell line with high metastatic potential
MDA-MB-231: human breast cancer cell line, highly invasive and highly metastatic (Ma et al, 2004) and a strong E2F transcriptional signature profile.
MCF7: human breast cancer cell line, low invasive and metastatic activities and dependent upon estrogen (Ma et al, 2004) and a weak E2F transcriptional signature profile.
T47D: human breast cancer cell line, poorly invasive in Boyden chamber assay and low metastatic potential in mice (Ma et al, 2004) and a weak E2F transcriptional signature profile.
HFFs: human foreskin fibroblasts, a kind from Dr. Jack Pledger, Moffitt Cancer Center.
MDA-MB-468: human breast cancer cell line, poorly invasive in Boyden chamber assay and low metastatic potential in mice.
SK-BR3: human breast cancer cell line, poorly invasive in Boyden chamber assay and low metastatic potential in mice (Ma et al, 2004) and a weak E2F transcriptional signature profile.
8226-s: human myeloma parental cell line ("s" stands for drug sensitive)
8226-dox40: drug-resistant derivative of 8226 which over expresses Pgp, obtained from Dr. Bill Dalton, Moffitt Cancer Center.
8226-MR20: drug-resistant derivative of 8226 which over expresses BCRP, a gift from Dr. Lori Hazlehurst, Moffitt Cancer Center.

Example I

Identification and Synthesis of the Therapeutic Compound

Grid-based Ligand Docking from Energetics (GLIDE, Schrödinger, Portland, Oreg.) was used to screen a 20,000 compound 3D chemical database (from ChemDiv, Inc) (see He Y, Armanious M K, Thomas M J, Cress W D. Identification of E2F-3B, an alternative form of E2F-3 lacking a conserved N-terminal region. Oncogene 2000; 19:3422-33; and Moberg K, Starz M A, Lees J A. E2F-4 switches from p130 to p107 and pRB in response to cell cycle reentry. Mol Cell Biol 1996; 16:1436-49) for putative interactions with the known crystal structure of the E2F4/DP2 heterodimer. Schrödinger's LigPrep 1.5 was used to convert a 2D structural database of these 20,000 compounds (obtained from ChemDiv as an MDL sdf file) into a database of 3D structures for virtual screening. During that process, LigPrep was instructed to maintain stereochemistry encoded in the sdf file, if present, but to generate all possible stereoisomers (with a limit of 32) for those structures for which stereochemical information was absent in the sdf file. For compounds containing multiple stereocenters, it was assumed that only relative stereochemistry was encoded in the original sdf file and that the physical compounds themselves were supplied as racemic mixtures; therefore enantiomeric partners of these structure were included in the 3D database. LigPrep was also instructed to generate alternative tautomers, ring conformations, and ionization states. The resulting database consisted of 70,913 3D structures. GLIDE 2.7 SP (Standard Precision mode) was then employed to dock each 3D structure to the E2F4 monomer, DP2 monomer and the E2F4/DP2 dimer.

Four-hundred small molecules emerged from the docking studies with predicted free energies ranging from −10.95 to −6.35 kcal/mol. These four hundred high scoring molecules were screened for the ability to inhibit E2F4 DNA-binding at 20 µM in standard E2F EMSAs. STAT3 EMSAs were used as negative control to insure that inhibition was E2F-specific (see Ma Y, Yuan J, Huang M, Jove R, Cress W D. Regulation of the Cyclin D3 Promoter by E2F1. J Biol Chem 2003; 278:16770-6). Incubation of these compounds with NIH-3T3 protein extracts identified ten compounds with potential E2F4-inhibitory activity. To measure activity against a human cancer cell line MCF-7 cells were treated with these ten compounds in culture and inhibition of E2F4 DNA-binding activity determined by EMSA.

Example II

Figures 10A, 10B:
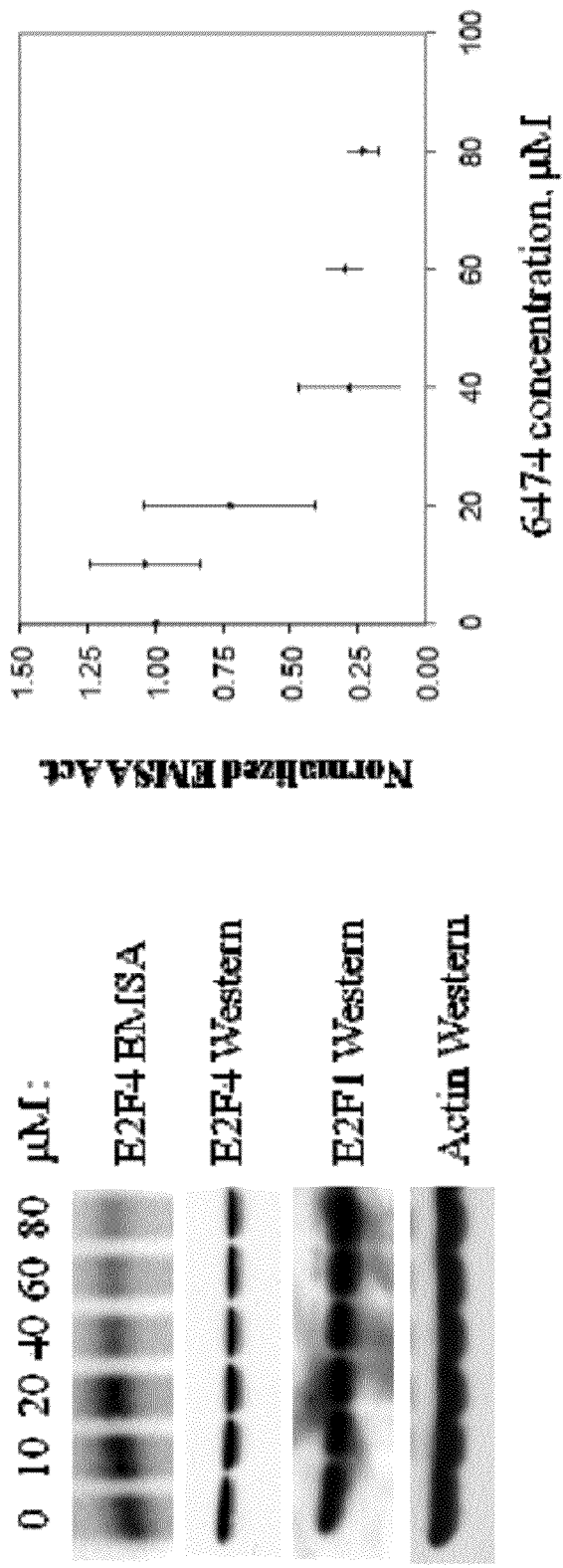
FIG. 10A: Western analyses results wherein human A375 melanocytes were treated for 9-hrs with the indicated concentration of the therapeutic compound. Whole cell extracts were prepared and total E2F4 activity determined by EMSA (top panel). The identity of the E2F4 complex is demonstrated in FIG. 3. Identical extracts were examined in westerns using the indicated antibodies to E2F4 and E2F1. The actin western serves as a loading control.
FIG. 10B: PhosphoImager EMSA results from multiple experiments are quantified and plotted. Signal intensities are normalized to the untreated sample. The error bars represent the standard deviation from the mean. Results reveal an in vivo $IC_{50}$ of 29.8 μM (±7.6 μM) for A375 cells.

The therapeutic compound inhibits E2F4 activity. Since the E2F/Rb pathway is disrupted in virtually ever case of melanoma, the inventors sought to determine whether HLM004674 would have activity in these cells. To this end, A375 cells, which represent a commonly used melanoma cell line, were treated for 9-hrs with various concentrations of the therapeutic compound to determine if the compound would have biological activity. Whole cell extracts of treated cells were prepared and the DNA-binding activity of E2F4 measured by EMSA. FIG. 10A demonstrates that at 10 and 20-µM concentrations the therapeutic compound has limited effect on E2F4 DNA-binding activity in A375 cells; however at 40-µM E2F4 inhibition is clearly apparent and increases at 60- and 80-µM concentrations. Since the observed loss of E2F4 DNA-binding activity could be the result of down regulation of E2F4 protein, the inventors performed Western blots on the same samples used for EMSA. The inventors found that 9-hrs of treatment with the therapeutic compound does not significantly affect the expression of E2F4 or E2F1— demonstrating that the diminished E2F4 signal observed by EMSA is not due to decreased protein expression. Likewise, the expression of E2F1 was not affected by the compound at 9-hrs. Actin served as a loading control in these experiments and in those that follow.

PhosphoImager EMSA signals from four independent experiments were quantified using ImageQuant and the results are graphed in FIG. 10B. The apparent $IC_{50}$ (drug concentration required to reduce total E2F4 DNA-binding activity by 50% of untreated cells was calculated using the Statistical Analysis System (Proc Probit)). Data indicate an $IC_{50}$ of 29.8 µM (±7.6 µM). In the examples that follow, 40-µM drug was used as standard HLM006476 concentration since that concentration of drug should reduce E2F4 activity by 50-75% and should limit off target effects.

Example III

Figure 11:
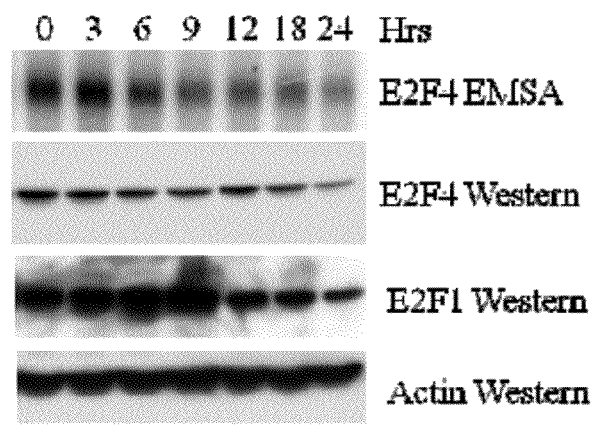
FIG. 11A: Western analyses results wherein A375 cells were treated with 40 μM of the therapeutic compound and EMSA performed at the indicated time intervals.
FIG. 11B: EMSA results from four independent experiments (as in 10A) were quantified and averages plotted as a function of time of treatment. The error bars represent the standard deviation from the mean.
Figure 11:
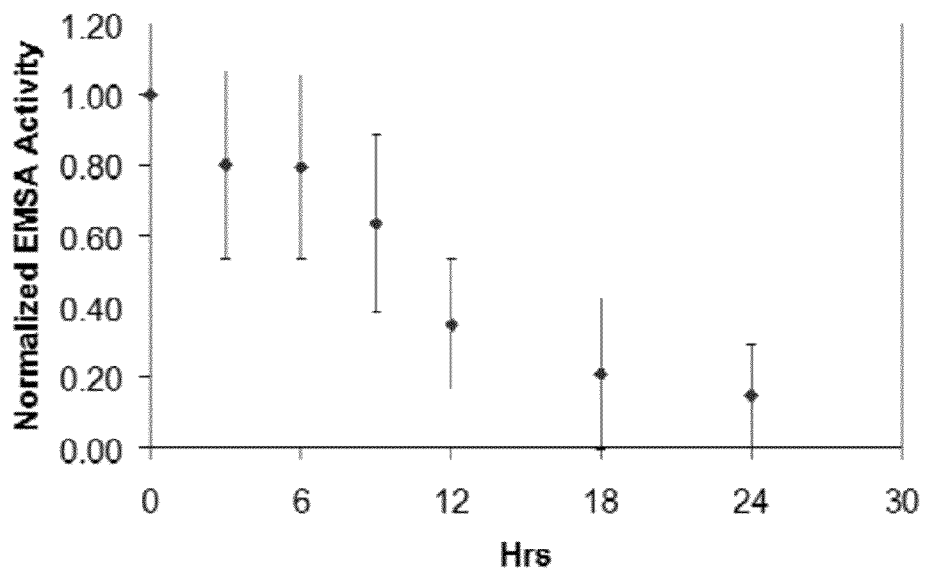

The therapeutic compound treatment leads to downregulation of total E2F4 protein. To determine the activity of the therapeutic compound over time, A375 cells were treated with 40-µM of compound and examined at 0-, 3-, 6-, 9-, 12-, 18- and 24-hrs by EMSA and western (FIG. 11A). With a single 40-µM dose, inhibition of E2F4 DNA-binding activity became apparent 9-hrs following treatment and persists for up to 24-hrs. By 24-hrs a decrease in total E2F4 protein became apparent—suggesting that inhibition of E2F4 DNA-binding may predispose E2F4 to degradation. The level of pro-apoptotic E2F1 rises at early time points, but is diminished at 24-hrs. EMSA activities from A375 cells treated with the therapeutic compound were quantified using ImageQuant and the results are plotted in FIG. 11B. This analysis indicates that half of the E2F DNA-binding activity is lost between 9- and 12-hrs after 40 µM the therapeutic compound treatment. The observation that the therapeutic compound down-regulates total E2F4 protein was surprising; however it may contribute to the lasting biological effect of the compound. Collectively, these data indicate that the therapeutic compound inhibits E2F4 activity through inhibition of its DNA-binding activity and down regulation of its expression.

Example IV

The therapeutic compound induces apoptosis. The data described herein strongly suggest that the therapeutic compound serves as an effective chemotherapeutic agent. To examine its effect on a range of commonly studied cell lines, the inventors utilized standard MTS assays to quantify cell viability following the therapeutic compound treatment. Cytotoxicity was determined using MTS assays, which were conducted using a CellTiter 96® AQueous One Cell Proliferation Assay Kit (Promega) following the published protocol. Cells in 0.1 ml volume were plated in triplicate into 96-well plates, $1 \times 10^4$ cells/well. the therapeutic compound was added and after 24 hours of incubation at 37° C., 20 µl of MTS dye was added to each well. Plates were read at 490 nm following 4 hrs MTS reaction time. The concentration of drug which produced a 50% inhibition of growth ($IC_{50}$) was calculated from linear regression analysis of the linear portion of the growth curves.

Figure 5:
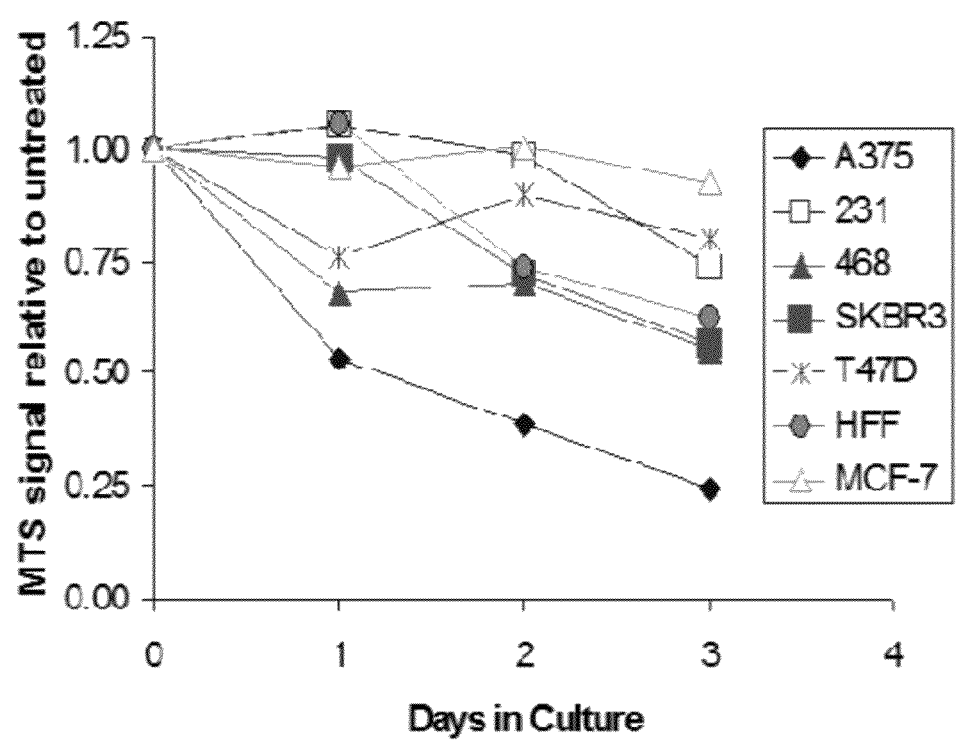
FIG. 5: The indicated cell lines growing exponentially in 96-well plates were treated with 40 μM HLM006474 and cellular proliferation/viability measured at 24-, 48- and 72-hrs after treatment using MTS. Each assay was performed in triplicate (error bars are not included to reduce clutter, A375 cells are the only cells with significantly affected at 40 μM).
Figure 6:
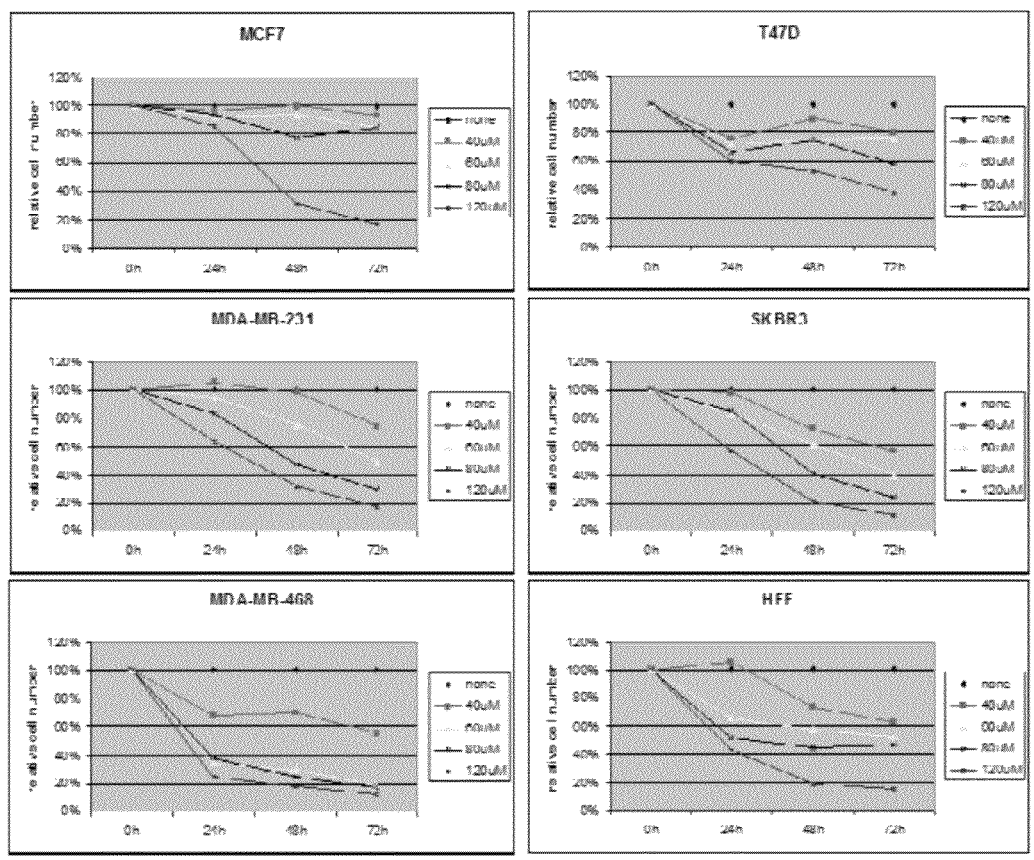
FIG. 6: Same as 5 except cells were treated with various concentrations of HLM006474, as indicated.
Figure 7:
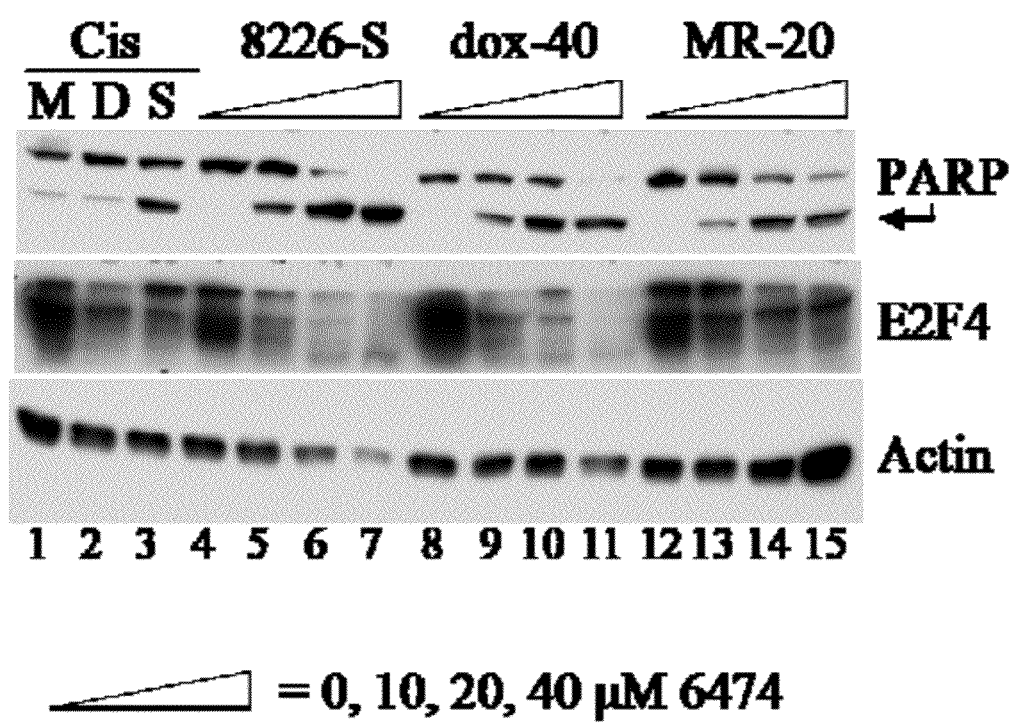
FIG. 7: HLM006474 induces apoptosis in multiple drug resistant cell lines. To determine if the therapeutic compound would be active in drug resistant cells a drug sensitive melanoma cell line 8226-s (S), and two drug-resistant derivative lines, 8226-dox40 (D) and 8226-MR20 (M), were treated with 10 μM cisplatin (lanes 1-3) or 0, 10, 20 or 40 μM HLM006474 as indicated by the triangle (lanes 4-15). Cells were collected 24 hours post drug exposure and extracts subjected to western blotting using antibodies to the indicated proteins. Cleavage of PARP indicates apoptosis. Minimal PARP cleavage following treatment with cisplatin reveals the drug-resistant nature of the 8226-dox40 (D) and 8226-MR20 (M) derivatives. In contrast, the cleavage of PARP following treatment with HLM006474 is very similar (the PARP response in MR-20 cells is slightly reduced) in the sensitive and resistant lines, indicating that HLM006474 may be active against cancer cells with drug resistance. MTS assays reveal a similar pattern. The $IC_{50}$ as measured by a MTS viability assay for the parental cell line 8226-s is 36±6 μM HLM006474. The $IC_{50}$ for the 8226-dox40 cell line is 31±4 μM and the $IC_{50}$ for the 8226-MR20 cell line is 46±6 μM HLM006474.
Figure 8:
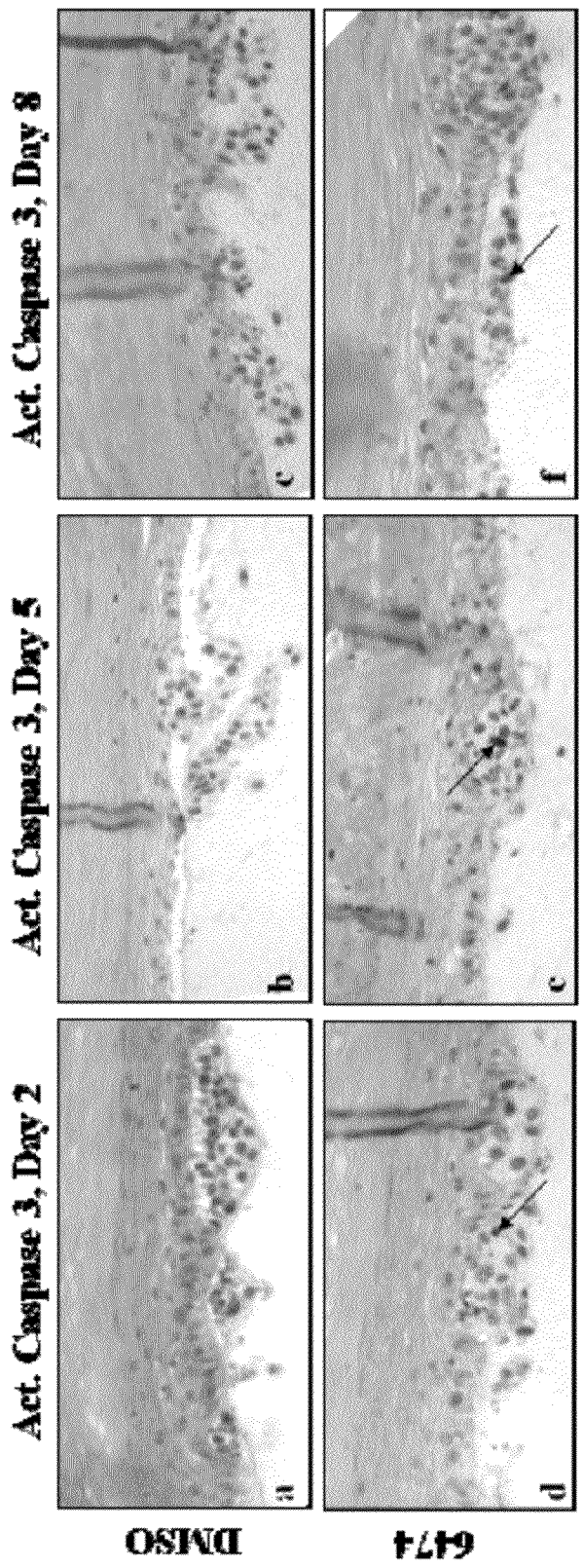
FIG. 8: Activated caspase 3 IHC was performed on thin sections of day 2, 5 and 8 treated with either DMSO (a-c) or 40 μM HLM006474 (d-f). Arrows point at darkly stained cells, which are rare in both control and HLM006474-treated tissues. These early timepoints were chosen because there are similar numbers of melanocytes present at early time points. Magnification, 200×. Data reveal that the HLM treatment results in no detectable increase in apoptotic cells.

The results of these assays clearly indicate that the therapeutic compound decreases the number of viable cells over the experimental time course (see FIGS. 5 and 6). In no case does the compound appear to increase proliferation, as might occur if depression of E2F activity would be sufficient to induce cellular proliferation.

To determine if treatment with the therapeutic compound contributes to apoptosis, Cells were detached from culture plates by trypsin treatment, washed twice with PBS, and fixed in 70% ethanol. Fixed cells were washed twice with PBS and treated with RNase A and propidium iodide (PI). PI staining was examined using a Becton-Dickinson FACScan instrument and Cell Quest software. TUNEL assay for apoptosis utilized a Pharmingen APO-BRDU Kit. MTS (3-(4,5-dimethylthiazol-2-yl)-5-(3-carboxymethoxyphenyl)-2-(4-sulfophenyl)-2H-tetrazolium, inner salt) assays were conducted using a CellTiter 96® AQueous One Cell Proliferation Assay Kit (Promega).

Figure 13:
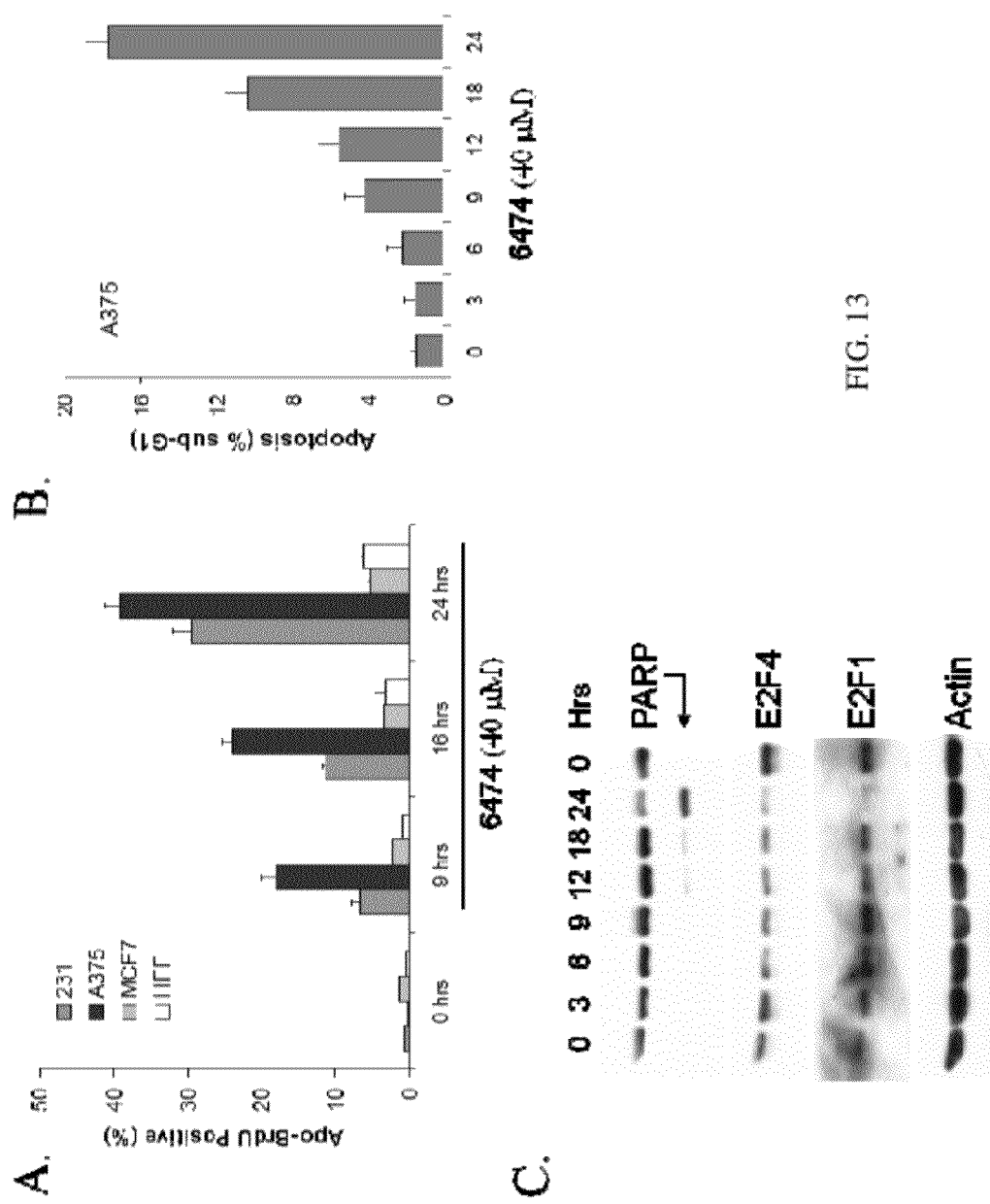
FIG. 13A: A375, MD-MBA-231 ("231"), MCF-7 and HFFs were treated with 40 μM HLM006474 for various times as indicated. Levels of apoptosis were determined using an Apo-BrdU TUNEL assay (BD Pharmingen).
FIG. 13B A375 cells were treated with 40 μM HLM006474 for various times as indicated. Levels of apoptosis were determined based upon sub-G1 DNA content.
FIG. 13C. A375 cells were treated as in 13B. Levels of PARP cleavage, E2F4, and E2F1 were determined by Western blotting. Actin served as a loading control.

A375, MDA-MB-231 (231), MCF-7 and human foreskin fibroblasts (HFF) cells were treated with 40-µM of the therapeutic compound for 24-hrs and subjected to a FACS based terminal deoxynucleotidyl transferase (TUNEL) assay (Apo-BrdU Kit from BD Pharmingen). FIG. 13a reveals a dramatic induction of apoptosis in the A375 and 231 cell lines. In contrast, the therapeutic compound did not induce an obvious increase in apoptosis in HFF or MCF-7 cells.

To further examine the timing of the therapeutic compound-induced apoptosis, A375 cells were treated with 40-µM the therapeutic compound, harvested and fixed at various time periods. Cells were then stained with propidium iodide to examine cell cycle status as estimated by flow cytometry. While no other obvious cell cycle effects were observed (data not shown) FIG. 13B highlights the significant increase in sub-G1 DNA content of the cells beginning approximately 9-hrs following the therapeutic compound treatment. Likewise, PARP cleavage (FIG. 13C) indicates significant apoptosis by 12-hrs following the therapeutic compound treatment. Thus, the therapeutic compound-induced apoptosis appears to temporally follow the down regulation of E2F4 DNA-binding and be largely coincident with E2F4 protein down regulation (FIG. 11B). Taken together, these results demonstrate that the therapeutic compound is a potent inducer of apoptosis in certain cell cancers.

Example V

The therapeutic compound treatment leads to apoptosis in a manner distinct from traditional chemotherapeutic drugs. To compare the mechanism of the therapeutic compound-induced apoptosis with that of several standard DNA damaging drugs, A375 cells were treated for 24-hrs with 40-µM the therapeutic compound, 10 µM cisplatin, 10 nM doxorubicin, 10 µM VP16 (etoposide) or with two-drug combinations. The inventors have previously shown that these chemotherapeutic drugs lead to a modest repression of E2F4 expression (in several cell lines), and that E2F4 deficiency leads to an increased susceptibility to the action of these drugs (Ma et al, 2004). FIG. 9 reveals that each of these drugs individually reduced E2F4 levels in A375 cells after 24-hrs of treatment. However, every two-drug combination essentially eliminated E2F4 expression; suggesting that the therapeutic compound may synergize with these various drugs in the elimination of E2F4 activity.

The inventors have previously shown that cyclin D3 promoter is upregulated upon serum stimulation dependent upon an E2F site at position −143 to −135 (Ma Y, Yuan J, Huang M, Jove R, Cress W D. Regulation of the Cyclin D3 Promoter by E2F1. J Biol Chem 2003; 278(19):16770-6). FIG. 9 reveals that the therapeutic compound treatment significantly reduces cyclin D3 protein expression, thus supporting the hypothesis that the therapeutic compound is blocking at least a subset of E2F-regulated genes. Treatment with the traditional chemotherapeutics cisplatin, doxorubicin and VP16, in contrast, had little effect on cyclin D3 (FIG. 9) or other cell cycle factors (data not shown). Westerns for PARP and the cleaved/activated form of PARP revealed that the therapeutic compound is a potent inducer of PARP cleavage, with no synergy between the therapeutic compound and the other drugs observed at these concentrations.

A Western against p53 was also performed to determine if p53 might play a role in the therapeutic compound-induced apoptosis (FIG. 9). As expected, the traditional chemotherapeutic agents each induced p53 expression; however the therapeutic compound did not (in fact, it may block p53 induction in A375 cells). Mcl-1, a pro-survival member of the Bcl-2 family, is known to be E2F regulated (see Croxton R, Ma Y, Cress W D. Differences in DNA binding properties between E2F1 and E2F4 specify repression of the Mcl-1 promoter. Oncogene 2002; 21:1563-70; Salama I, Malone P S, Mihaimeed F, Jones J L. A review of the S100 proteins in cancer. Eur J Surg Oncol 2007). Western blots for Mcl-1 suggest that the therapeutic compound may slightly repress Mcl-1 in A375 cells. These results suggest that apoptosis induced by the therapeutic compound acts through a mechanism distinct from other traditional chemotherapies and may therefore be useful in malignancies that have become resistant to drugs that function through these pathways.

Figure 14A:
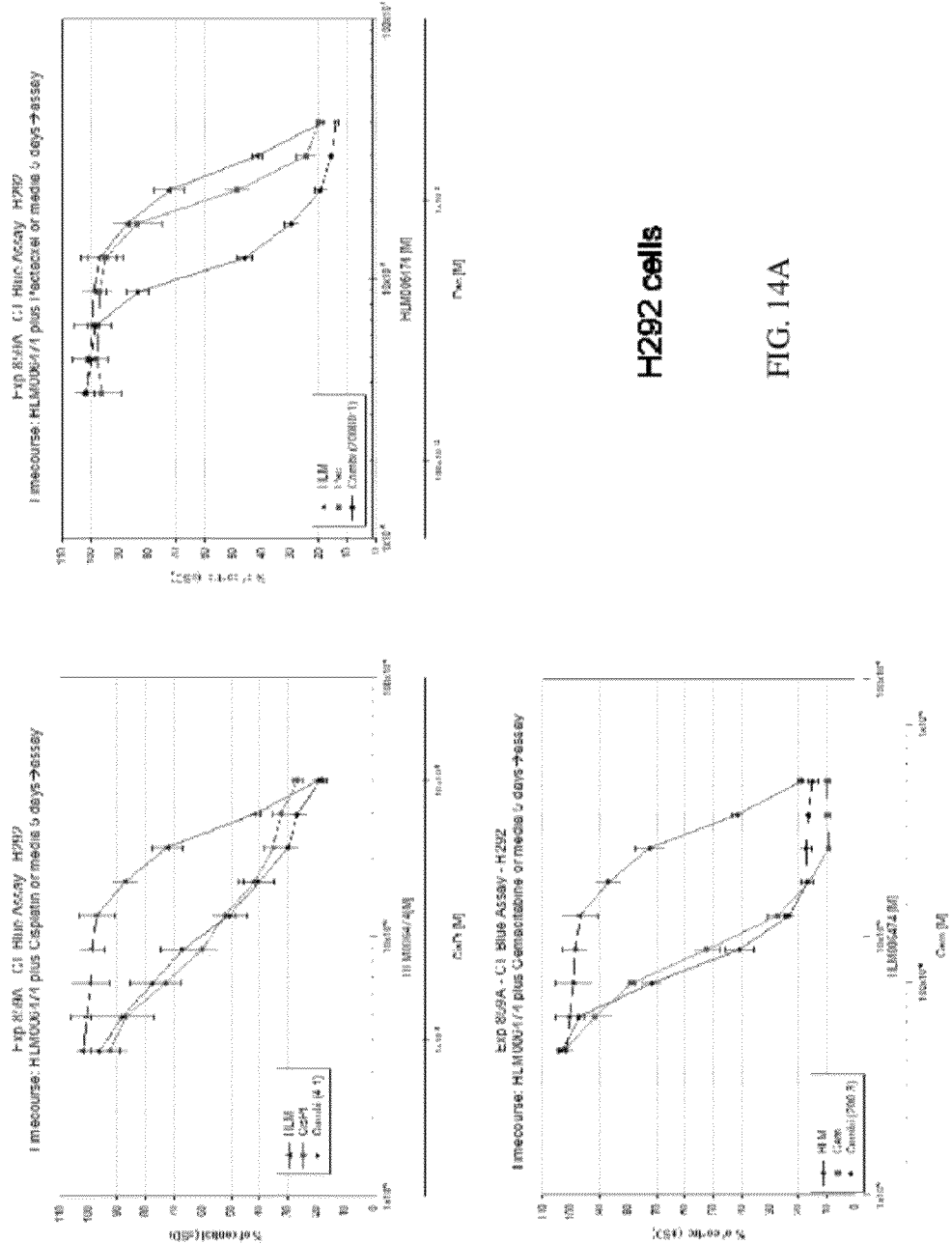
FIGS. 14A-14C: Viability assays show that the therapeutic compound synergizes significantly with taxol, but to a lesser degree with cisplatin or gemacitabine. The indicated lung cancer cell lines were exposed to taxol, cisplatin, or gemacitabine alone, the therapeutic compound alone, or a combination as indicated. These experiments and analysis were performed in the Experimental Therapeutics Core using the CT Blue Viability Assay.
Figure 14B:
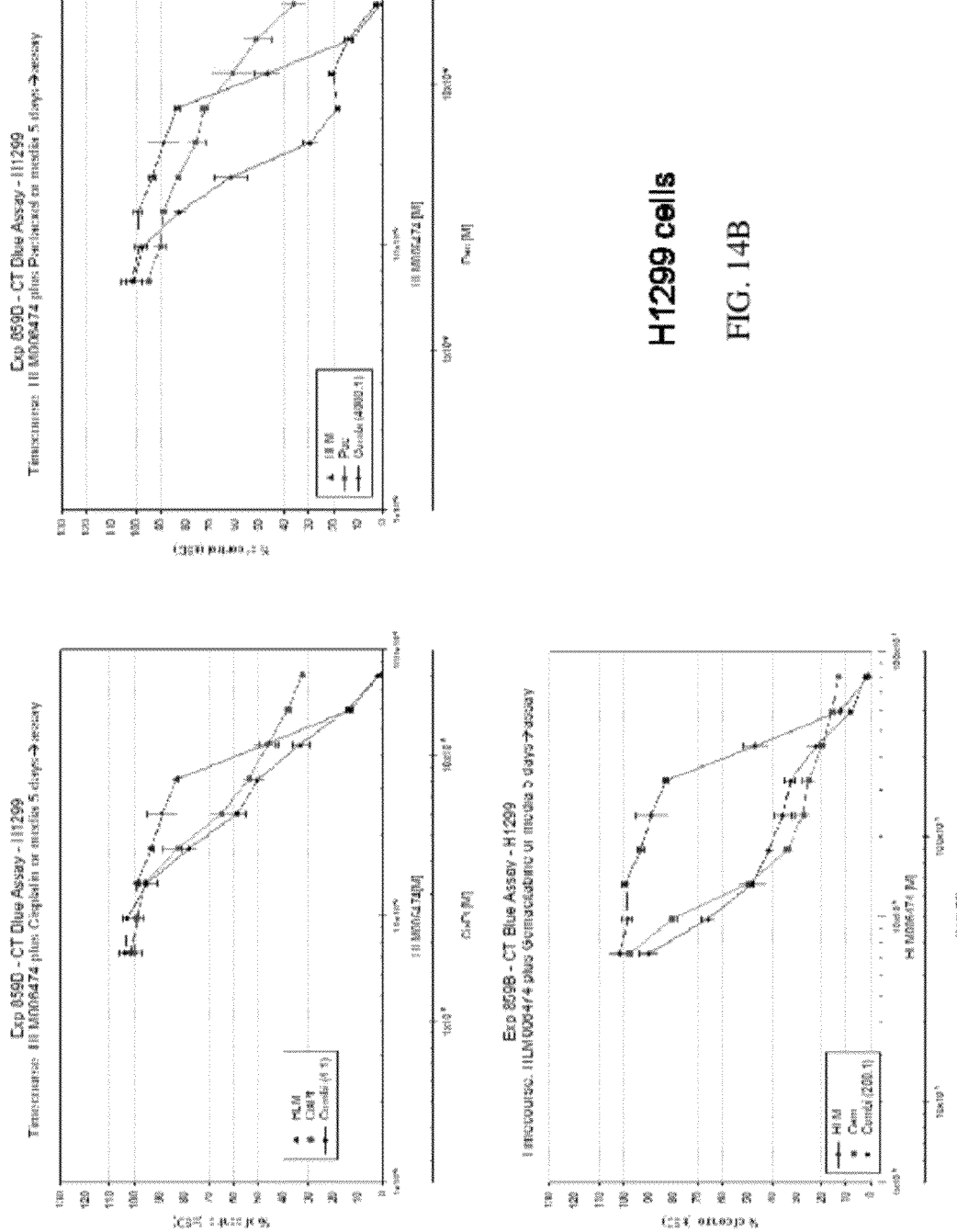
Figure 14C:
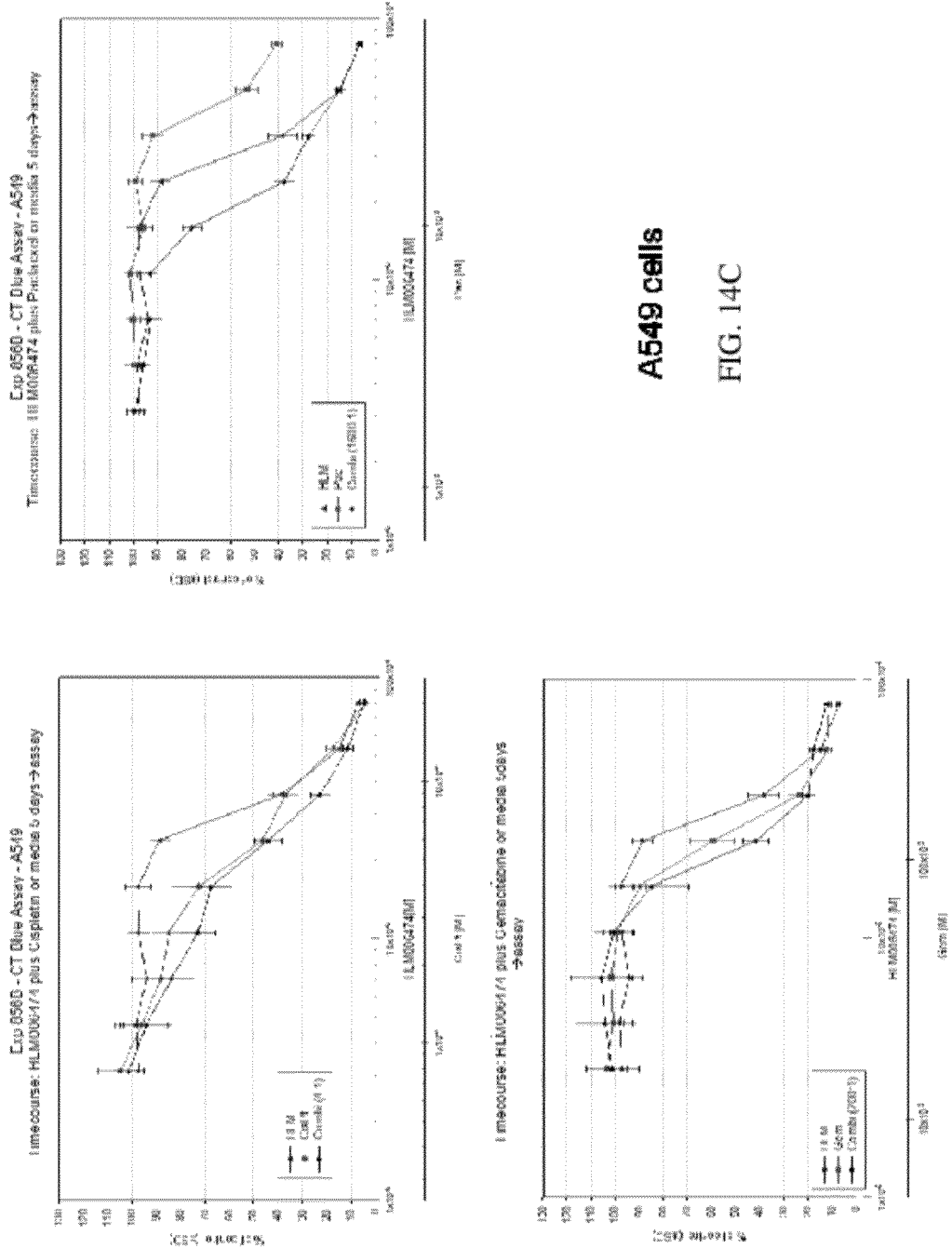

Therefore, the therapeutic compound also has efficacy for treatment based on its synergy with other common chemotherapeutic drugs. The therapeutic compound has also been tested for its ability to synergize with a number of chemotherapeutic drugs. The inventors examined the synergy between the therapeutic compound and three drugs commonly used in lung cancer treatment; cisplatin, gemacitabine and taxol. FIGS. 14A-14C demonstrates that the therapeutic compound synergizes significantly with taxol, but to a lesser degree with cisplatin or gemacitabine.

Example VI

Figure 12:
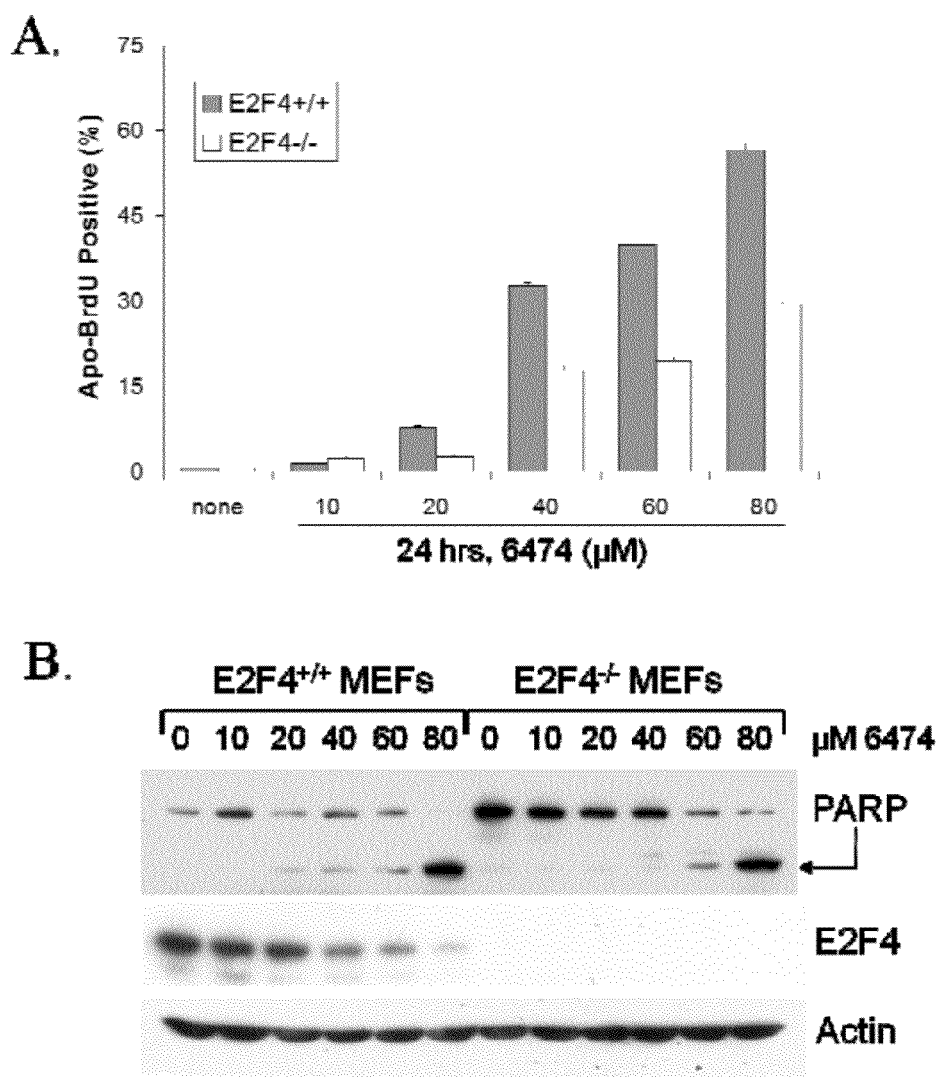
FIG. 12A: MEFS derived from sibling WT and E2F4$^{-/-}$ mice were treated for 24-hrs with the indicated doses of HLM006474. Apoptosis was determined using ApoBrdU (BD Pharmingen).
FIG. 12B: MEFS derived from sibling WT and E2F4$^{-/-}$ mice were treated as in A subjected to western blotting using a PARP antibody or E2F4 antibody. PARP cleavage (as indicated by the arrow) is an independent measure of apoptosis.

The therapeutic compound activity is partially dependent on E2F4. To determine if the effect of the therapeutic compound is dependent upon E2F4, the inventors compared the therapeutic compound response of immortalized MEFs derived from E2F4-deficient mice with MEFS derived from wildtype siblings. FIG. 12A demonstrates that the therapeutic compound induces a two-fold increase in the level of apoptosis in WT cells as compared to that of E2F4-deficient cells. These same E2F4-deficient MEFs are more sensitive to every other drug that the inventors have ever tested (Ma et al., 2004), thus the resistance to the therapeutic compound is even more convincing. The finding that E2F4-null MEFs are affected by the therapeutic compound suggests that E2F4 is not the sole target and that down regulation of additional E2Fs likely contributes to cell death. This is consistent with the biochemical evidence (FIGS. 3 and 4) that the therapeutic compound inhibits all E2F family members. FIG. 12B demonstrates that PARP cleavage is evident in E2F4 proficient MEFs even as low as 20 µM the therapeutic compound, whereas 60 µM the therapeutic compound is required to detect PARP cleavage in E2F4-deficient MEFs. Collectively, these data indicate that apoptosis induced by the therapeutic compound is in part dependent on E2F4.

Example VII

The therapeutic compound inhibits A375 proliferation in a three-dimensional model system. Given the biological and biochemical response of A375 cells to the therapeutic compound in cell culture, the inventors postulated that this compound may inhibit malignant growth in a three-dimensional skin model of A375 invasion. Culture inserts of differentiated full-thickness 3D skin reconstruction model of A375 melanoma cells were purchased from MatTek (Ashland, Mass.). These were prepared by culturing mixed suspensions of normal human epidermal keratinocytes and A375 cells (1:10 ratio) on fibroblast contracted collagen gels and allowing differentiation for approximately one week in serum free media to form a 3D skin-like structure. These cultures were treated with 0, 40 or 80 µM 6474 and harvested after 0, 2, 5, 8, 12, 16 and 20 days.

In this model, the highly metastatic A375 melanocytes were mixed with normal human keratinocytes and seeded on fibroblast-contracted collagen gels. The mixed cells were then induced to differentiate in serum free media to form three-dimensional, highly differentiated, full thickness skin-like tissues. After seven days of differentiation the cells were then treated with 0 (DMSO carrier alone), 40 or 80 µM the therapeutic compound. The three-dimensional models were then cultured for 2, 5, 8, 12, 16 and 20 days. At the appointed time, 3D cultures were fixed in formalin, paraffin embedded, sectioned and either stained with H&E or processed for immunohistochemistry (1HC) using antibodies against S-100 to measure expression of a melanocyte marker, E2F4 to determine if it were down regulated as in 2D culture, activated caspase-3 to measure apoptosis and Ki-76 to measure the proliferative index.

Figure 15A:
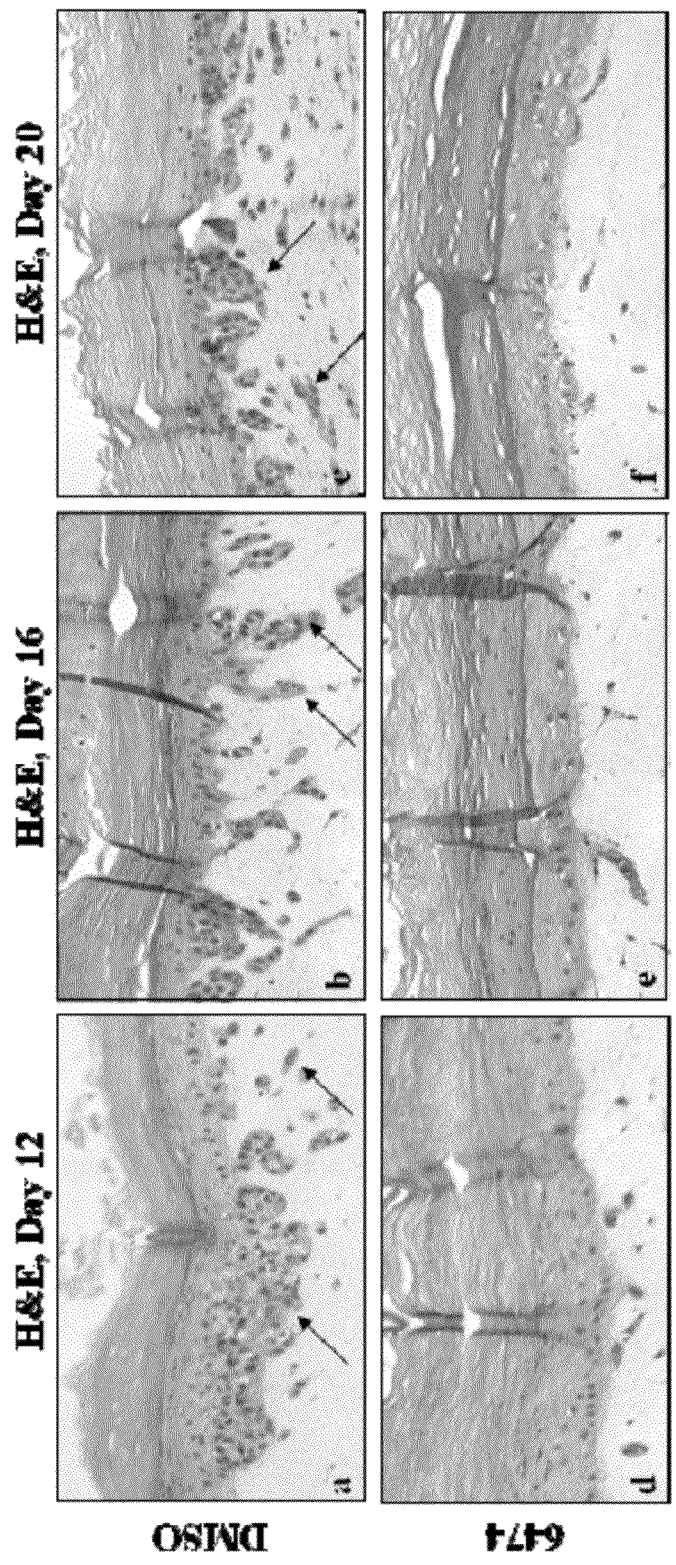
FIG. 15A: H&E staining was performed on thin sections of day 12, 16 and 20 tissues treated with either DMSO (a-c) or 40 μM HLM006474 (d-f). Magnification, 100×. The top bright red layer represents the epidermis, the next layer of cells with dark blue nuclei represent the melanocyte layer and the bottom largely unstained area represents the fibroblast contracted collagen dermal substrate. Arrows in the DMSO only cells indicate cells and cell clusters that have invaded the dermal layer that are largely absent in the HLM006474 treated tissues.

FIG. 15A highlights the H&E stain of tissues over time in the absence and presence of the therapeutic compound. Due to space limitations, the results of 80 µM the therapeutic compound treatment are not shown herein (there is essentially no melanocyte proliferation at 80 µM). In this figure, the keratinocytes form the upper epidermal layer, with the second distinct layer of cells representing the melanocytes. In the early time points this layer is only a few cells thick, and these cells are distinguished by their dark nuclear staining. The third distinct layer represents the fibroblast contracted collagen which makes up the underlying dermal substrate. Over time, the metastatic melanocytes proliferate and form nodes, which grow and invade the underlying collagen substrate. This growth and invasion is clearly evident in the DMSO treated samples.

Figure 15B:
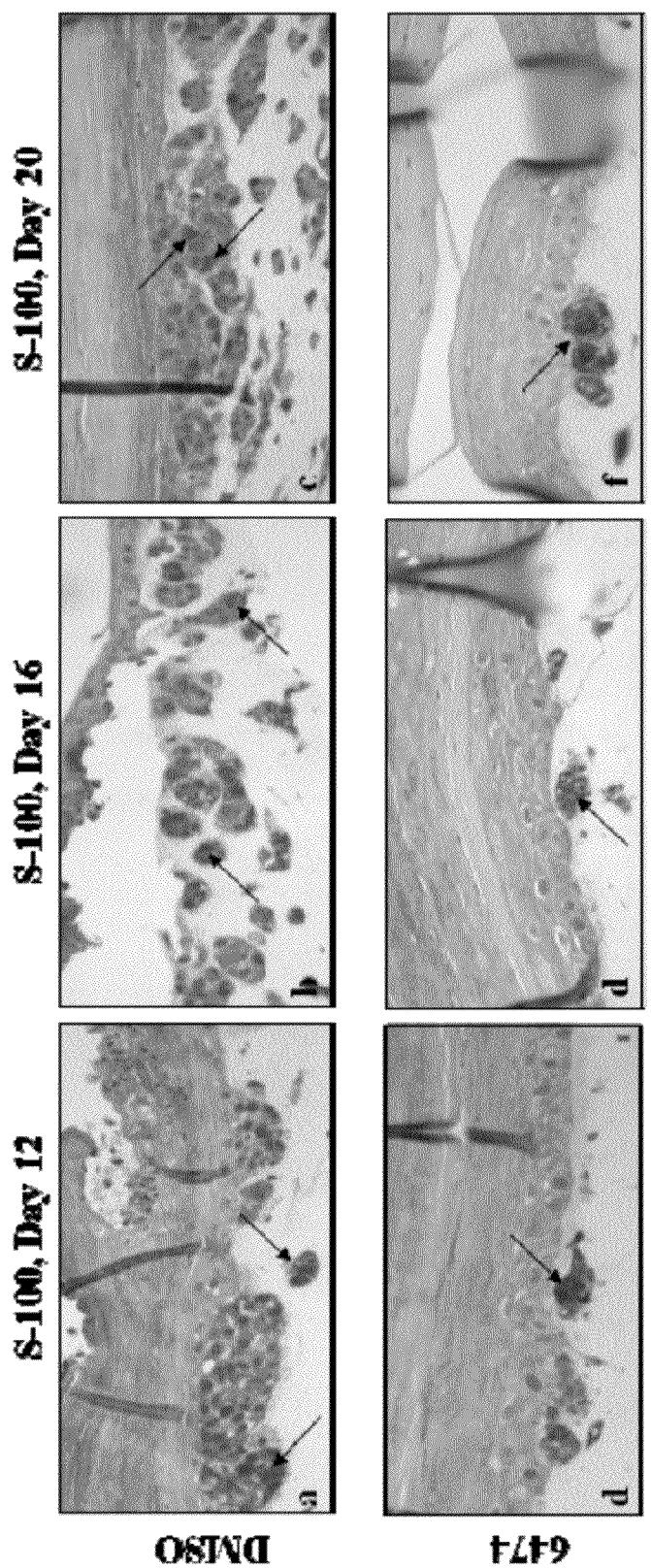
FIG. 15B: S100 IHC was performed as in Panel A. Magnification, 200×. Arrows point at S-100 positive cells, which are very rare in the HLM006474-treated tissue.

To confirm the presence and growth of melanocytes the tissues were subjected to IHC with a melanocyte marker (S-100, see FIG. 15B). FIG. 15B reveals strong expression of S-100 in control treated cells. In contrast, only a few S-100 positive cells are observed in the therapeutic compound-treated tissues; making it clear that the therapeutic compound significantly inhibited the proliferation and subsequent invasion of the melanocytes into the collagen layer. Since a reduction in S-100 expression is considered an excellent marker for the successful treatment of melanoma (Verona R, Moberg K, Estes S, et al. E2F activity is regulated by cell cycle-dependent changes in subcellular localization. Mol Cell Biol 1997; 17:7268-82), these results suggest that the therapeutic compound is a highly effective inhibitor of malignant growth in this model system. The compound had no obvious deleterious effects on the other cells (fibroblasts and keratinocytes) making up the 3D tissue.

Figure 15C:
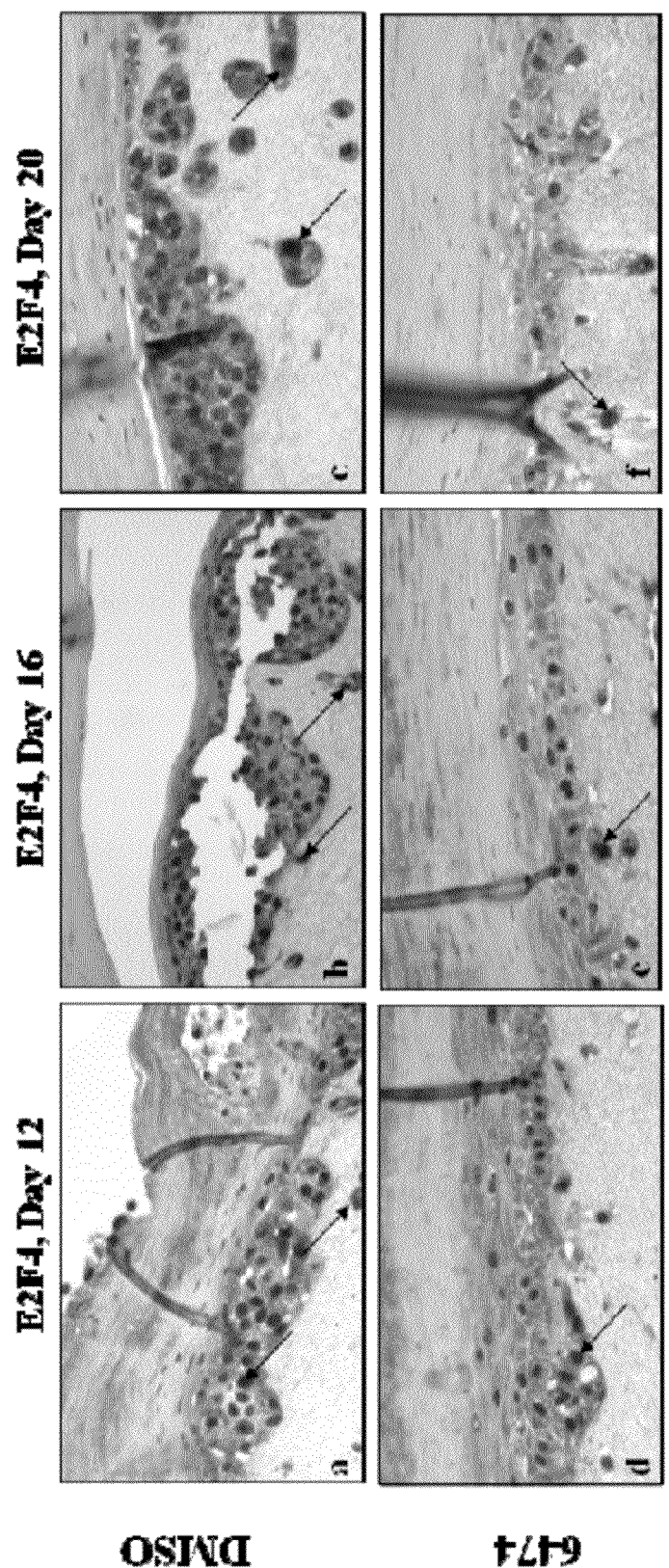
FIG. 15C: E2F4 IHC was performed on thin sections as in Panel A. Magnification, 200×. Arrows point at darkly stained nuclei and lightly stained cytoplasm, which are rare in the HLM006474-treated tissues.
Figure 15D:
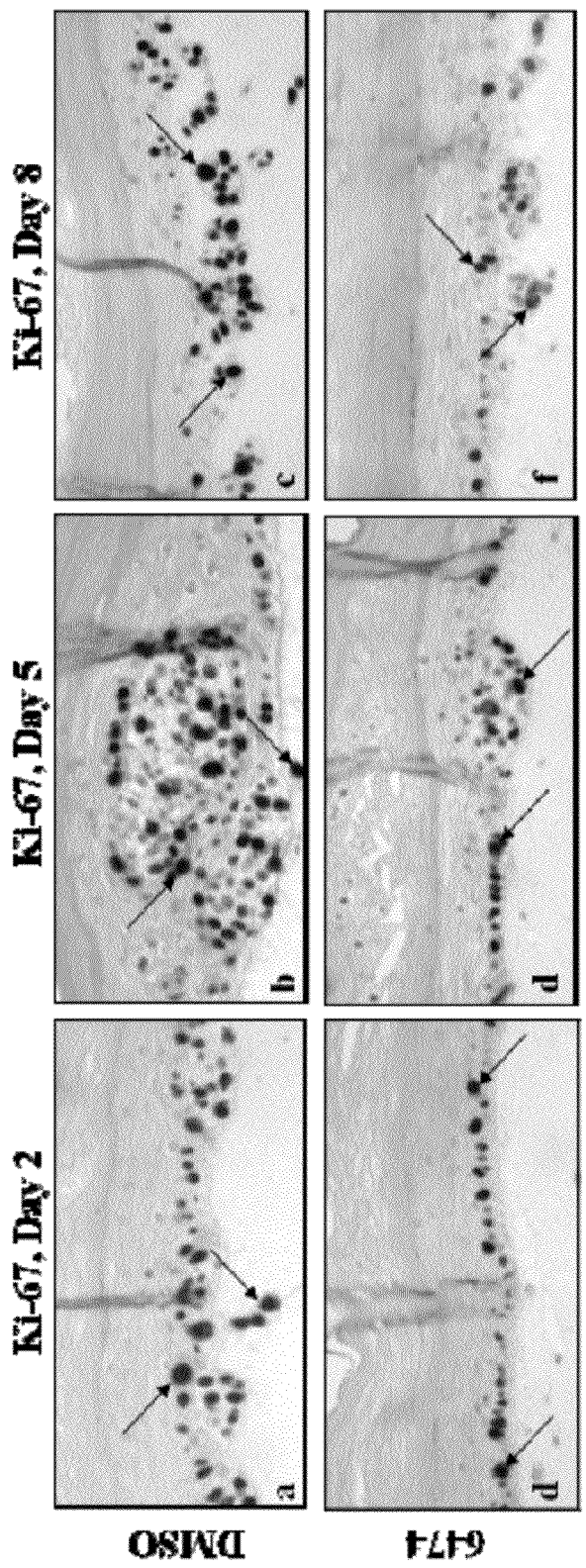
FIG. 15D: Ki-67 IHC was performed on thin sections of day 2, 5 and 8 treated with either DMSO (a-c) or 40 μM HLM006474 (d-f). Magnification, 200×.

Westerns of cells treated with the therapeutic compound in two-dimensional cultures indicated that the compound led to significant down regulation of the E2F4 protein. To determine if E2F4 was reduced in three-dimensional culture, sections were subjected to E2F4 IHC. FIG. 15C reveals that E2F4 levels are clearly reduced in the treated tissues. Although there are less total cells in the HLM006774 treated tissue (which slightly complicates direct comparisons) it is clear that a lower fraction of the therapeutic compound-treated cells stain positively for E2F4, and of those that are positive the staining is generally less intense. Finally, it is noted that in the treated tissues the remaining E2F4 is predominantly nuclear, whereas in the untreated cells a fraction of E2F4 is also located in the cytoplasm. Since E2F4 is known to shuttle between the cytoplasm (G1/S) and nucleus (G0/G1) during the cell cycle, this result may primarily reflect a quiescent state in the therapeutic compound-treated cells (Harbour J W, Dean D C. Rb function in cell-cycle regulation and apoptosis. Nat Cell Biol 2000; 2:E65-7). These results indicate that the therapeutic compound is likely hitting its intended target in the 3D culture.

To determine whether the inhibition of invasion and melanocyte proliferation was due to increased apoptosis sections were stained with a marker for apoptosis (activated-caspase 3). No difference was observed in samples day 12, 16, or 20, and as such the inventors stained earlier time point reasoning that apoptosis might be an early event that would eliminate cells that would later invade the collagen substrate. FIG. 15 reveals that no significant difference activated caspase-3 positive cells was observed even in the day 2, 5 or 8 tissues. These data do not fully rule out a possibility for apoptosis in the 3D culture model; however, since it is possible that these dying cells are simply hard to detect. To determine whether an inhibition of cell division might account for inhibition of melanocyte proliferation, tissue sections were stained with a proliferative marker (Ki-67, FIG. 15D). The Ki-67 staining clearly reveals a decrease in the number of proliferative cells when treated with the therapeutic compound. Thus, the therapeutic compound's most obvious mode of action in the 3D model is in the inhibition of proliferation.

Example VIII

Electrophoretic mobility shift assays (EMSAs) were performed utilizing 20 µg of whole cell extract and an $^{32}$P-labeled oligonucleotide probe, as previously described. Antibodies used in supershift experiments were: E2F4 (mouse monoclonal 2-12E8(21), gift from J. Lees, MIT), Rb (Calbiochem; OP28), p107 (Santa Cruz Biotechnology; SC-318x), p130 (Santa Cruz Biotechnology; SC-317x), E2F1 (Santa Cruz Biotechnology; SC-193x), E2F2 (Santa Cruz Biotechnology; SC-633x), E2F2 (NeoMarkers, MS-264-s), E2F3 (Santa Cruz Biotechnology; SC-879x), E2F3 (Santa Cruz Biotechnology; SC-878x). EMSA signals were captured with a Storm PhosphoImager and band intensities quantified with ImageQuant Software. Quantitative EMSA assays were performed in triplicate. Western blots utilized 50 µg of whole cell extract per lane as previously described. Primary antibodies used in these studies consisted of E2F4 (Santa Cruz Biotechnology; SC-1082), E2F1 (Santa Cruz Biotechnology; SC-251), 8-actin (Sigma; A5441), PARP (Cell Signaling; #9542), cyclinD3 (BD Pharmingen; 14781A), cyclinA (monoclonal gift from E. Leof, Mayo Clinic Cancer Center), p53 (BD Pharmingen; 554293), Bax (Santa Cruz Biotechnology; SC-493), Mcl-1 (Santa Cruz Biotechnology; SC-819), p107 (Santa Cruz Biotechnology; SC-318), and p130 (Santa Cruz Biotechnology; SC-317). Detection of proteins was accomplished using horseradish-peroxidase-conjugated secondary antibodies and enhanced chemiluminescence (ECL) purchased from Amersham.

Double-stranded oligonucleotides probes were used for EMSAs. The sequences used were (the central E2F recognition site is underlined):

Oligonucleotides

```
wt A-    ATT TAA GTT TCG CGC CCT TTC TCA A wt B-    TTG AGA AAG GGC GCG AAA CTT AAA T

Mut A-   ATT TAA GTT TCG ATC CCT TTC TCA A

Mut B-   TTG AGA AAG GGA TCG AAA CTT AAA T
```

Oligonucleotides were first annealed and then labeled using the Klenow fragment of DNA polymerase and alpha-labeled dATP and TTP.

Example IX

Figure 16:
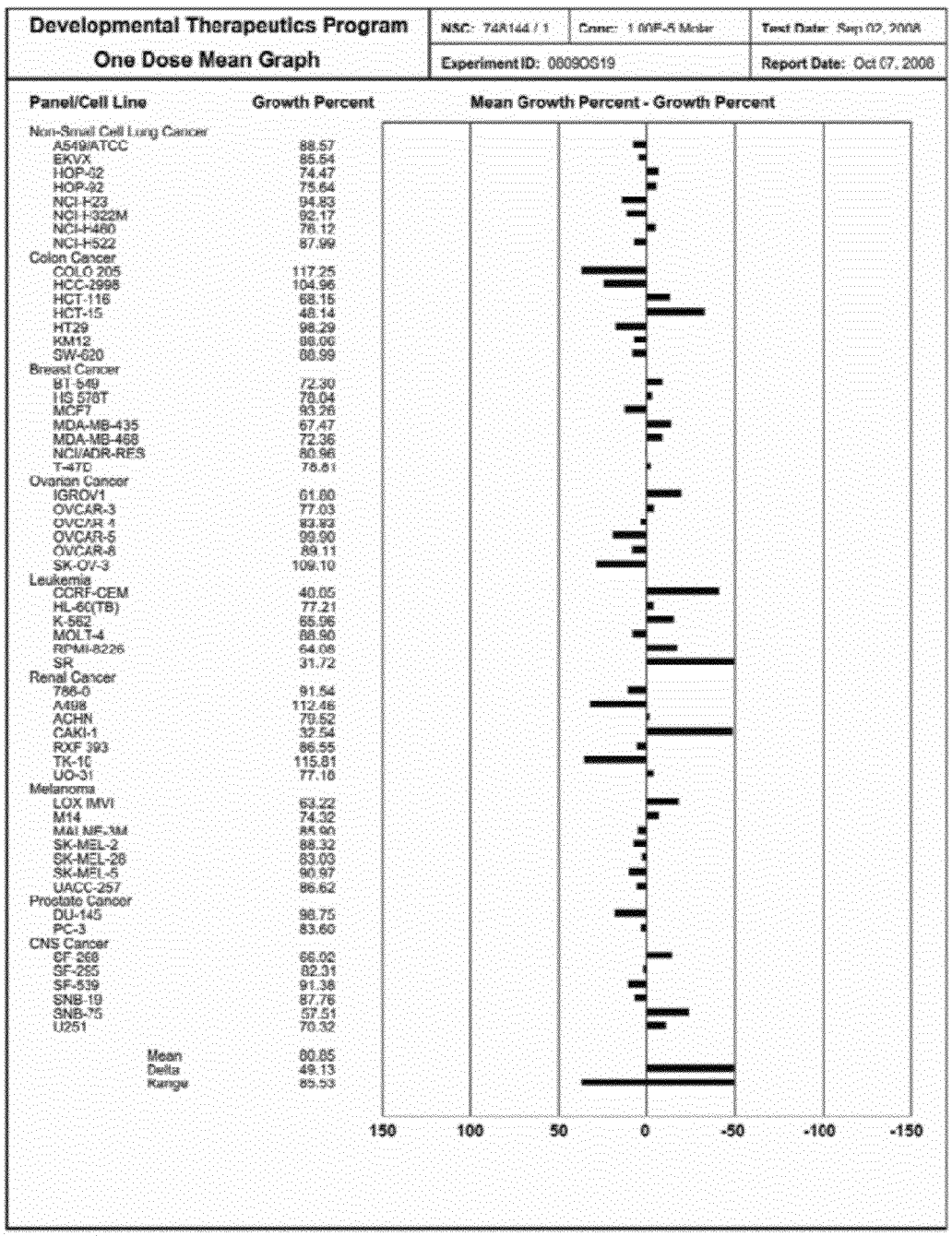
FIG. 16: HLM006474 was submitted to the National Cancer Institutes Developmental Therapeutic Program NCI60 Drug Screening Program. The drug concentration used is below the known IC50 of HLM004647 of 30 micromolar, but is the NCI standard concentration. Results are reported as mean growth percent less growth percent. Cell lines in which the drug is most effective therefore yield a negative growth value in the figure. In spite of being slightly below the IC50 a number of cell lines were significantly growth inhibited by HLM006474. As a whole, Leukemia cell lines were the most sensitive group.

The therapeutic compound inhibited growth in numerous cancer lines. The therapeutic compound was submitted to the NCI60 drug screen. FIG. 16 highlights the results. The drug concentration used is below the known IC50 of HLM004647 of 30 micromolar, but is the NCI standard concentration. In spite of being slightly below the IC50 a number of cell lines were significantly growth inhibited by the therapeutic compound. As a whole, leukemia cell lines were the most sensitive group.

Example X

Figure 17:
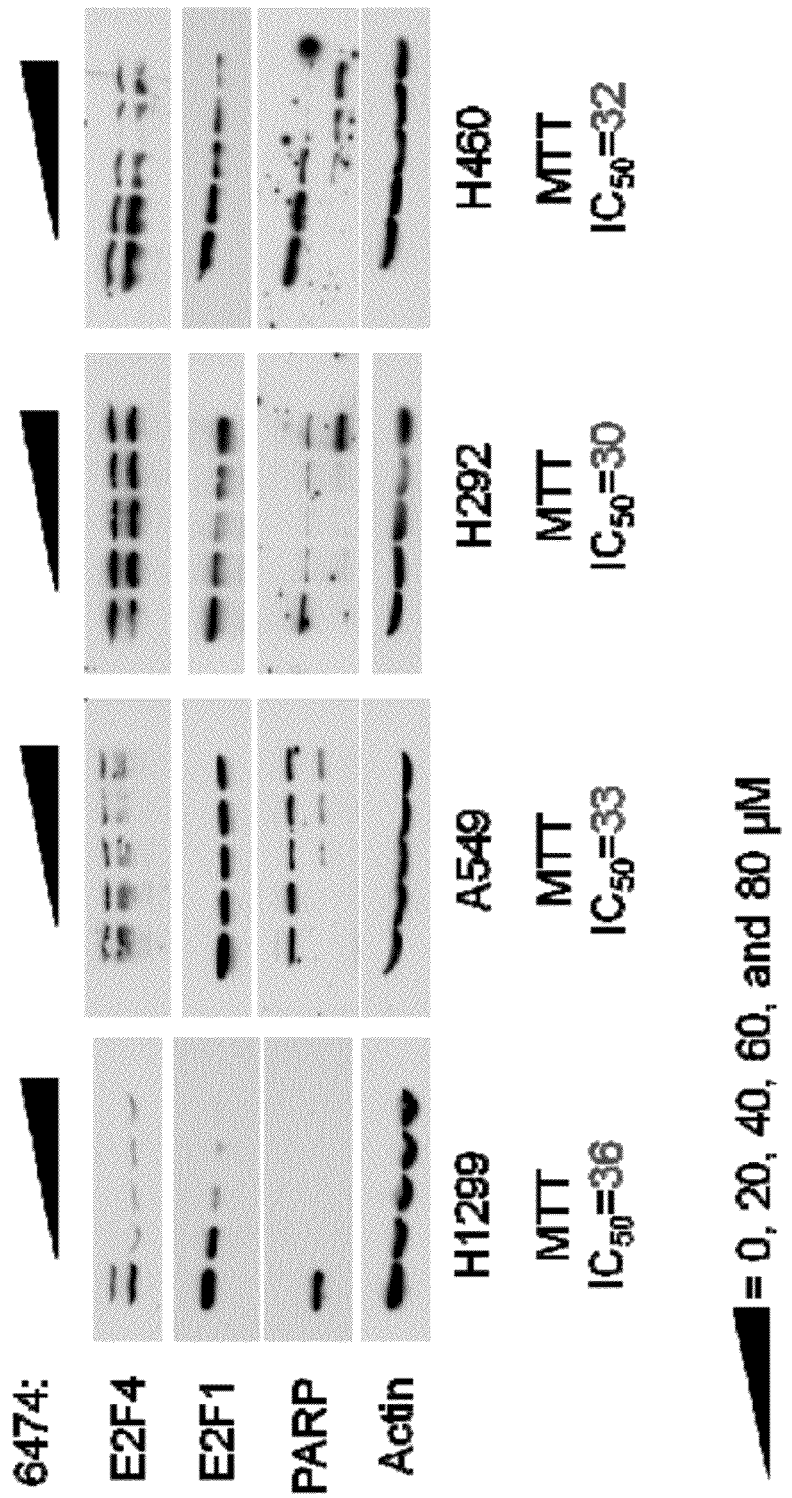
FIG. 17: The therapeutic compound treatment leads to varied downregulation of the E2F1 and E2F4 proteins in NSCLC lines. The indicated lines were treated with various concentrations of the therapeutic compound and subjected western blotting 24 hrs later using the indicated antibodies. The IC50 for growth inhibition determined by MTT assay is shown for each line demonstrating that there is not a strong correlation between E2F4 downregulation and sensitivity to the drug.

The therapeutic compound treatment leads to dramatic downregulation of various cell cycle proteins. The inventors previously found that the therapeutic compound treatment led to the down regulation of the E2F4 protein DNA (Ma et al., 2008) in A375 cells. In order to further examine the mechanism of action of the therapeutic compound four lung cancer cell lines were treated with various concentrations of drug and western blots performed on cell extracts after 24 hr. FIG. 17 reveals that the four cell lines differ in their response to the therapeutic compound. H1299 and H460 cells demonstrate evidence that they are very sensitive to the drug showing clear downregulation of the E2F1 and E2F4 proteins as well as cleavage of PARP (indicating the induction of apoptosis). A549 and H292 cells demonstrate only a limited sensitivity to the therapeutic compound indicating some PARP cleavage, but no dramatic reduction in E2F1 or E2F4.

Figure 18:
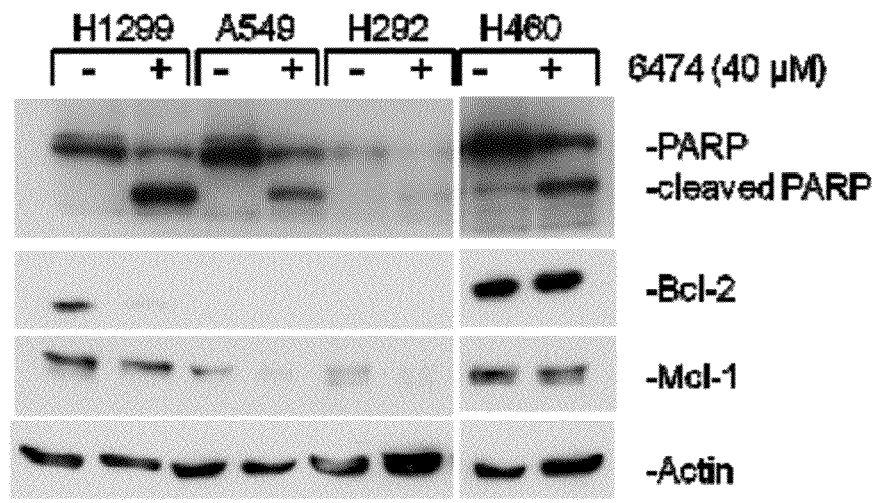
FIG. 18: The therapeutic compound treatment leads to varied downregulation of anti-apoptotic Bcl-2 family members Bcl-2 and Mcl-1. The indicated lines were treated with 40 micromolar the therapeutic compound and subjected western blotting 24 hrs later using the indicated antibodies.

The inventors next examined this group of cell lines for various apoptotic and cell cycle markers at a single dose of 40-µM of the therapeutic compound (just above it biochemical IC50). In H1299 cells, the most sensitive of the five lines, the therapeutic compound treatment led to significant downregulation of Bcl-2, but no change in Mcl-1 (see FIG. 18). In contrast, A549 and H292 cells (which clearly lack Bcl-2) both demonstrated downregulation of Mcl-1. Surprisingly, the H460 cells which are clearly drug sensitive did not show changes in either Bcl-2 or Mcl-2 demonstrating that the therapeutic compound-induced apoptosis is not necessarily mediated by either Bcl-2 or Mcl-1.

Figure 19:
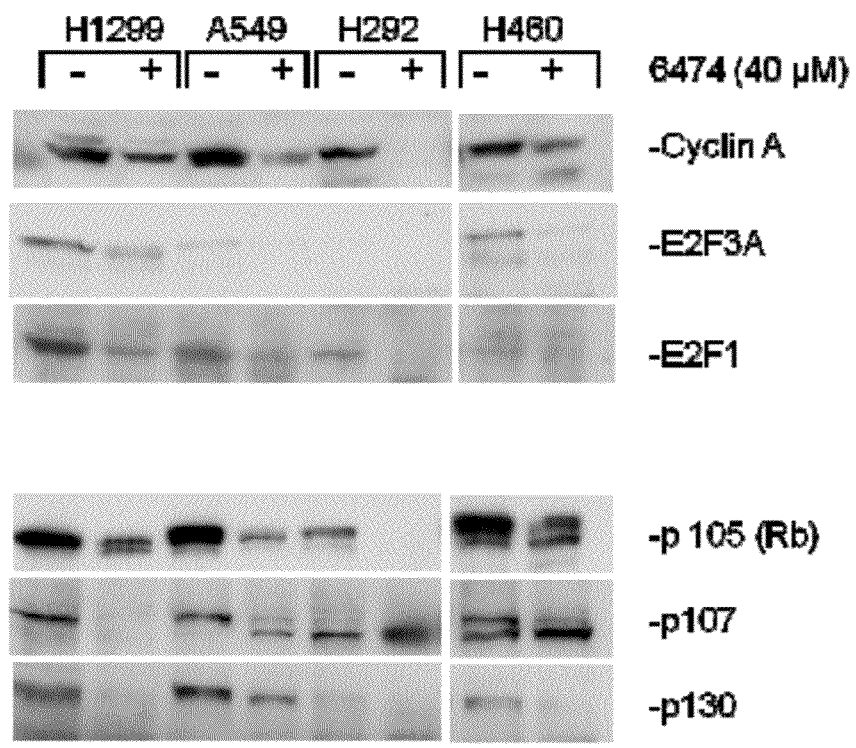
FIG. 19: The therapeutic compound treatment leads to downregulation of many positive and negative cell cycle regulatory proteins in NSCLC lines. The indicated NSCLC lines were treated with 40 micromolar the therapeutic compound and subjected western blotting 24 hrs later using the indicated antibodies.

Examination of proliferative cell cycle markers (FIG. 19) generally yielded the expected findings. Cyclin A, E2F1 and E2F3A which are all considered E2F-driven markers for S phase were clearly down regulated in all cells sensitive to the drug. H358 cells showed no decrease in cyclin A or E2F1 and only a modest decrease in E2F3A consistent with their resistance to the therapeutic compound. Surprisingly, however a number of negative cell cycle regulators where dramatically down regulated following the therapeutic compound treatment. The best example is Rb which is down (at least modestly) in every cell line treated. Rb family members, p107 and p130, largely follow suite. Given that the therapeutic compound blocks cell cycle progression this finding is very surprising.

Figure 20:
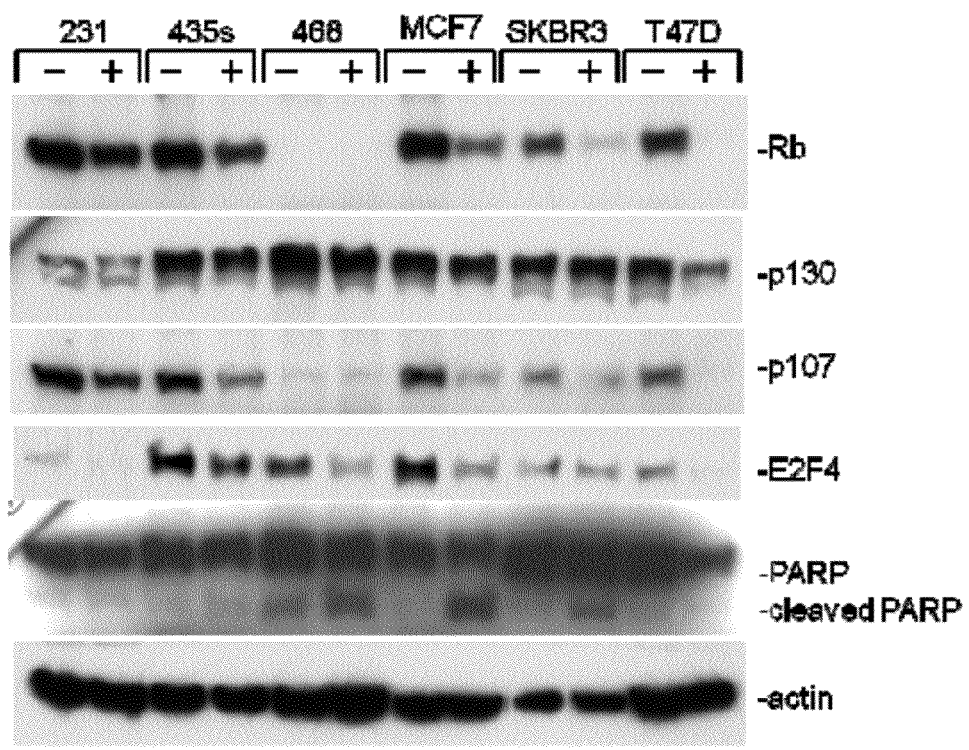
FIG. 20: The therapeutic compound treatment leads to downregulation of Rb family members in breast cancer cell lines at the proteins level. The indicated breast cancer lines were treated with 40 micromolar the therapeutic compound and subjected western blotting 24 hrs later using the indicated antibodies.
Figure 21:
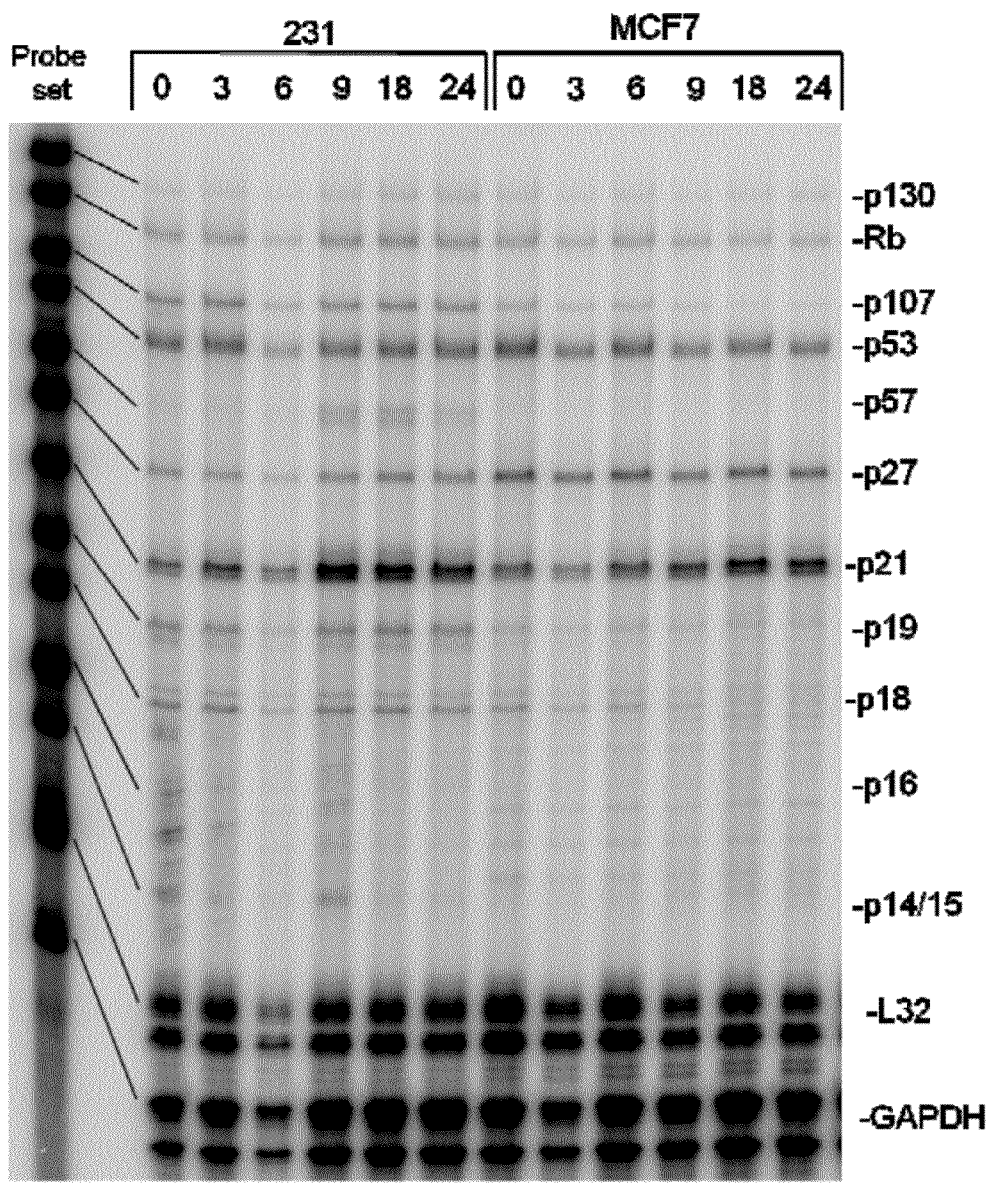
FIG. 21: The therapeutic compound treatment does not down regulate Rb at the transcriptional level. The indicated breast cancer lines were treated with 40 micromolar the therapeutic compound and subjected RNAse protection assay 24 hrs later using the indicated probes. Since there is no change in message the therapeutic compound treatment may affect the rate of Rb protein synthesis or degradation.

Given the surprising nature of the finding in lung cancer cells the inventors also examined a series of breast cancer cell lines. FIG. 20 reveals a similar pattern as observed in lung cancer cell lines both Rb and p107 proteins are dramatically down regulated in certain cell lines. Previous reports have demonstrated that Rb family member can be regulated transcriptionally by E2F. An RNase protection assay was performed to determine if downregulation of the Rb family members at the level of mRNA could account for the downregulation of the proteins. Two breast cancer cell lines were examined at 0, 3, 6, 9, 18 and 24 hr following the therapeutic compound treatment (FIG. 21). The first line represented 231 cells, which did not respond to drug, and the other line represented MCF7 cells, which responded robustly. The mRNA for p107 was indeed repressed in the sensitive MCF7 cells and not the insensitive 231 cells. However, there was no significant change in either cell line of Rb at the mRNA level, demonstrating that the therapeutic compound is having its potent affect on Rb post-transcriptionally. Of the other cell cycle markers that happened to be included in the RPA probeset p21 was found to be upregulated in both cell lines, whereas p57 was upregulated detectably only in 231 cells. The mRNA levels of p130, p57, p27, p19, p16 and p14/15 were not detectably altered by the therapeutic compound treatment in either cell line.

Example XI

Figure 22:
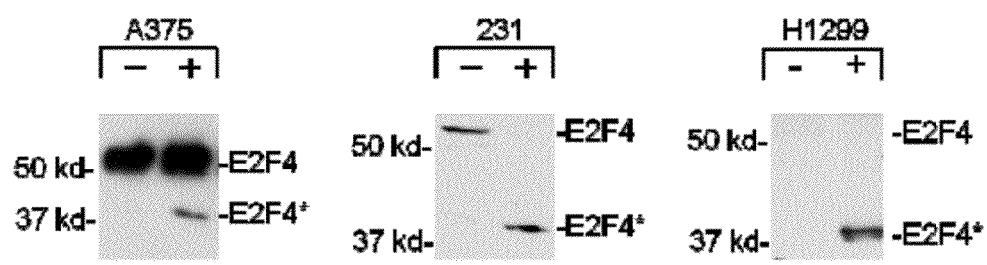
FIG. 22: Evidence that the therapeutic compound treatment leads to cleavage of the E2F4 protein. The indicated cell lines were treated with 40 micromolar the therapeutic compound and subjected to western blotting 24 hrs later. In this case, the entire lanes were subjected to western blot with an E2F4 antibody in order to detect potential immunoreactive truncation products. In every case a 40 kD immunoreactive band appears after the therapeutic compound treatment. It is hypothesized that this band represents an E2F4 cleavage product.

The therapeutic compound treatment induces an apparent E2F4 cleavage. The inventors were unable to inhibit the downregulation of E2F4 following the therapeutic compound treatment using proteasome inhibitors, therefore the inventors examined a second candidate mechanism that E2F4 might be downregulated by proteolytic cleavage. For this experiment cells were treated with 40 uM the therapeutic compound and were subjected to western blotting. However, rather than cut the western membrane into three pieces (to probe simultaneously for three proteins of different sizes) the entire membrane was used to reveal smaller immunoreactive bands. FIG. 22 reveals that the therapeutic compound treatment indeed results in the appearance of a 40 kD band that may represent a proteolytic cleavage of E2F4.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of modulating E2F activity in a cell, comprising contacting the cell with a small molecule inhibitor having the formula:

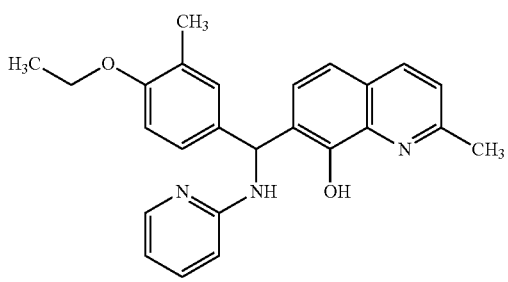

or a pharmaceutically acceptable salt thereof.

2. The method of claim 1, wherein the cell is contacted with between about 40 μM and 80 μM of the small molecular inhibitor.

3. A method of treating a proliferative cellular disorder, comprising the step of administering a therapeutically effective amount of a small molecule inhibitor having the formula:

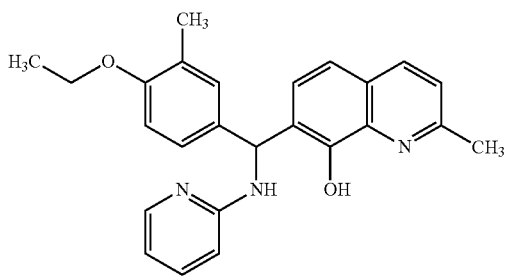

or a pharmaceutically acceptable salt thereof to a subject in need of said treatment, wherein the proliferative cell disorder is characterized by a disruption of the E2F/Rb pathway.

4. The method of claim 3, wherein proliferative cellular disorder is selected from the group consisting of melanomas, renal cancer, CNS cancer, leukemia, ovarian cancer, breast cancer, colon cancer and non-small cell lung cancer.

5. The method of claim 3, wherein the small molecular inhibitor is co-administered with at least one compound selected from the group consisting of doxorubicin, VP16 (etoposide), taxol, cisplatin and gemacitabine.

6. The method of claim 3, wherein between about 40 μM and 80 μM of the small molecular inhibitor is administered to the subject.

7. A method of down-regulating total E2F4 protein in a cell, comprising contacting the cell with a small molecule inhibitor having the formula:

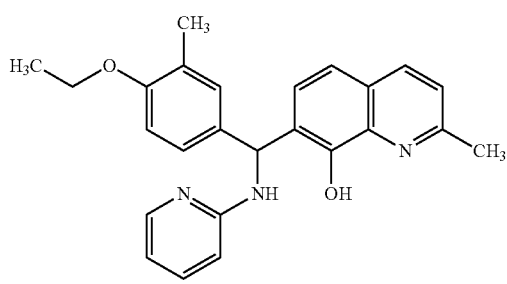

or a pharmaceutically acceptable salt thereof.

8. The method of claim 7, wherein the cell is contacted with between about 40 μM and 80 μM of the small molecular inhibitor.

9. A method of inducing apoptosis in a cell, comprising contacting the cell with a small molecule inhibitor having the formula:

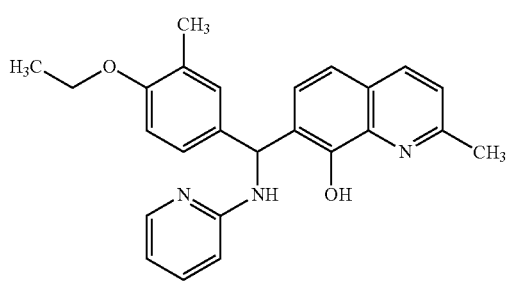

or a pharmaceutically acceptable salt thereof.

10. The method of claim 9, wherein the cell is contacted with between about 40 μM and 80 μM of the small molecular inhibitor.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: artificial organism
<220> FEATURE:
<223> OTHER INFORMATION: wt A oligo

<400> SEQUENCE: 1
atttaagttt cgcgcccttt ctcaa                                      25

<210> SEQ ID NO 2
<211> LENGTH: 25
<212> TYPE: DNA
<213> ORGANISM: artificial organism
<220> FEATURE:
<223> OTHER INFORMATION: wt B oligo

<400> SEQUENCE: 2
ttgagaaagg cggcgaaact taaat                                      25

<210> SEQ ID NO 3
<211> LENGTH: 25
<212> TYPE: DNA
```

```
<213> ORGANISM: artificial sequence
<220> FEATURE:
<223> OTHER INFORMATION: Mut A

<400> SEQUENCE: 3
atttaagttt cgatcccttt ctcaa                               25

<210> SEQ ID NO 4
<211> LENGTH: 25
<212> TYPE: DNA
<213> ORGANISM: artificial sequence
<220> FEATURE:
<223> OTHER INFORMATION: Mut B

<400> SEQUENCE: 4
ttgagaaagg gatcgaaact taaat                               25
```